United States Patent
Suzuki

(10) Patent No.: US 10,383,522 B2
(45) Date of Patent: Aug. 20, 2019

(54) PULSE LASER AND PHOTOACOUSTIC APPARATUS

(71) Applicant: CANON KABUSHIKI KAISHA, Tokyo (JP)

(72) Inventor: Koichi Suzuki, Kodaira (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 30 days.

(21) Appl. No.: 14/315,075

(22) Filed: Jun. 25, 2014

(65) Prior Publication Data
US 2015/0005612 A1   Jan. 1, 2015

(30) Foreign Application Priority Data
Jun. 28, 2013 (JP) ................. 2013-136918

(51) Int. Cl.
| | | |
|---|---|---|
| *A61B 5/00* | (2006.01) | |
| *H01S 3/10* | (2006.01) | |
| *H01S 3/091* | (2006.01) | |
| *H01S 3/092* | (2006.01) | |
| *H01S 3/102* | (2006.01) | |

(Continued)

(52) U.S. Cl.
CPC ............ *A61B 5/0095* (2013.01); *H01S 3/092* (2013.01); *H01S 3/0912* (2013.01); *H01S 3/106* (2013.01); *H01S 3/1024* (2013.01); *H01S 3/10069* (2013.01); *H01S 3/115* (2013.01)

(58) Field of Classification Search
CPC .................................................. H01S 3/0912
See application file for complete search history.

(56) References Cited

U.S. PATENT DOCUMENTS 3,806,829 A * 4/1974 Duston .............. B23K 26/0622
                                                          219/121.61
4,644,550 A * 2/1987 Csery ...................... A61F 9/008
                                                          372/10

(Continued)

FOREIGN PATENT DOCUMENTS

CN      102258386 A    11/2011
EP       0989640 A2 *  3/2000  .............. H01S 3/117

(Continued)

OTHER PUBLICATIONS

Srirang Manohar et al. "Region-Of-Interest Breast Studies Using the Twente Photoacoustic Mammoscope (PAM;" Proc. of SPIE; vol. 6437; Feb. 7, 2007; pp. 643702-1 thru 643702-9; XP055107398.

*Primary Examiner* — Joshua King
(74) *Attorney, Agent, or Firm* — Canon U.S.A., Inc. IP Division

(57) ABSTRACT

A pulse laser includes a laser medium, a charge storage unit, a power source unit configured to supply an electrical charge to the charge storage unit, an excitation unit configured to cause irradiation of the laser medium with excitation light onto the laser medium by being supplied the electrical charge stored in the charge storage unit, a switching unit configured to repeatedly supply the charge stored in the charge storage unit to the excitation unit, an energy monitoring unit configured to monitor energy stored in the charge storage unit, and a control unit configured to prevent the switching unit from supplying the electrical charge stored in the charge storage unit to the excitation unit when the energy monitored by the energy monitoring unit is larger than a threshold.

19 Claims, 10 Drawing Sheets

(51) Int. Cl.
*H01S 3/106* (2006.01)
*H01S 3/115* (2006.01)

(56) References Cited

U.S. PATENT DOCUMENTS

| | | | | |
|---|---|---|---|---|
| 5,315,607 | A * | 5/1994 | Nielsen | H01S 3/092 |
| | | | | 372/25 |
| 6,084,897 | A * | 7/2000 | Wakabayashi | H01S 3/134 |
| | | | | 372/33 |
| 6,324,196 | B1 * | 11/2001 | Desor | H01S 3/225 |
| | | | | 372/25 |
| 6,370,174 | B1 * | 4/2002 | Onkels | G03F 7/70025 |
| | | | | 372/38.04 |
| 6,421,362 | B1 * | 7/2002 | Matsunaga | H01S 3/0975 |
| | | | | 320/161 |
| 6,442,181 | B1 * | 8/2002 | Oliver | G03F 7/70025 |
| | | | | 372/25 |
| RE38,054 | E * | 4/2003 | Hofmann | C23C 14/0694 |
| | | | | 372/25 |
| 8,594,144 | B1 * | 11/2013 | Bagg | F41G 3/145 |
| | | | | 372/25 |
| 2002/0044587 | A1 * | 4/2002 | Oliver | G03F 7/70025 |
| | | | | 372/58 |
| 2002/0154668 | A1 * | 10/2002 | Knowles | G03F 7/70025 |
| | | | | 372/55 |
| 2003/0012234 | A1 * | 1/2003 | Watson | G03F 7/70025 |
| | | | | 372/25 |
| 2003/0138019 | A1 * | 7/2003 | Rylov | H01S 3/225 |
| | | | | 372/58 |
| 2007/0071047 | A1 * | 3/2007 | Huang | H01S 3/097 |
| | | | | 372/38.02 |
| 2007/0230520 | A1 * | 10/2007 | Mordaunt | A61F 9/008 |
| | | | | 372/23 |
| 2012/0033689 | A1 * | 2/2012 | Targsdorf | H01S 3/09702 |
| | | | | 372/25 |
| 2013/0308668 | A1 * | 11/2013 | Guskov | H01S 5/0428 |
| | | | | 372/38.04 |

FOREIGN PATENT DOCUMENTS

| | | | | |
|---|---|---|---|---|
| GB | 2149199 A | 6/1985 | | |
| JP | 63-153875 A | 6/1988 | | |
| JP | H01-93188 A | 4/1989 | | |
| JP | 7-115238 A | 5/1995 | | |
| JP | H07-154013 A | 6/1995 | | |
| JP | 2714166 B2 * | 2/1998 | | H01S 3/097 |
| JP | 2000-014679 A | 1/2000 | | |
| JP | 2000-503164 A | 3/2000 | | |
| JP | 2003-163395 A | 6/2003 | | |
| JP | 2011-224205 A | 11/2011 | | |
| JP | 2012-084630 A | 4/2012 | | |

* cited by examiner

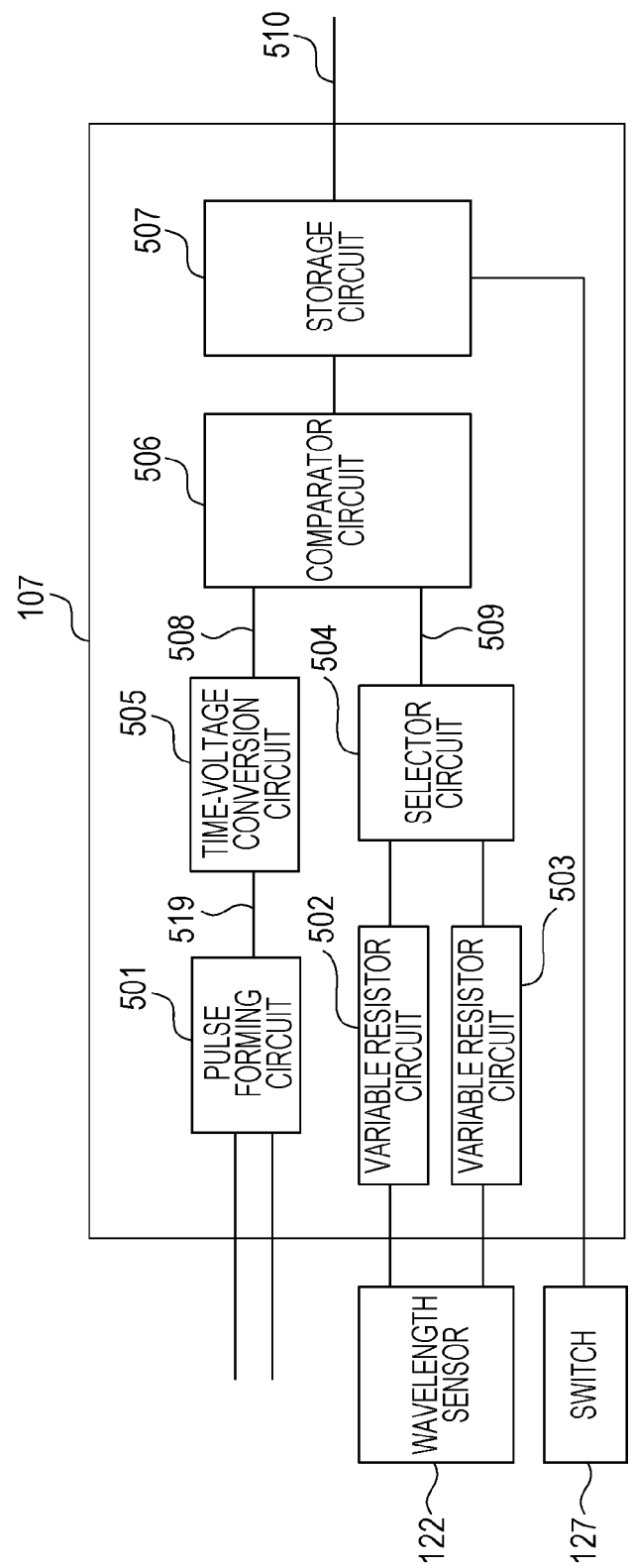

PULSE LASER AND PHOTOACOUSTIC APPARATUS

BACKGROUND OF THE INVENTION

Field of the Invention

The present invention relates to a pulse laser and photoacoustic apparatus configured to emit light pulses repetitiously.

Description of the Related Art

Photoacoustic apparatuses that emit light from a pulse laser onto a subject and use a probe to receive photoacoustic waves generated from inside the subject, to obtain information on the form and function of the interior of the subject are widely researched in the medical field. When applying such a photoacoustic apparatus to biological subjects, the intensity of the light irradiated onto the biological subject must be controlled so as to not be more than a predetermined safe threshold. This threshold is known as the maximum permissible exposure (MPE). The intensity of light emitted from such a pulse laser may be controlled depending on the objective.

Japanese Patent Laid-Open No. 63-153875 discloses an example of a method to control the intensity of light emitted from a pulse laser. Japanese Patent Laid-Open No. 63-153875 discloses a method in which current flowing to a lamp for exciting a laser medium and the voltage applied to this lamp is detected to obtain a value for the power input to the lamp. Japanese Patent Laid-Open No. 63-153875 discloses a method to control the power value next input to the lamp so that this value stays within a predetermined range on the basis of the obtained power value.

SUMMARY OF THE INVENTION

However, according to the method disclosed in Japanese Patent Laid-Open No. 63-153875, power must be input to the lamp before the driving of the lamp can be controlled. For this reason, the lamp can excite the laser medium before control is performed by emitting light, which creates a problem that undesired light may potentially be generated from the laser medium. The intensity of this undesired light has the potential to be outside the predetermined range.

According to the present specification, a pulse laser is provided in which undesired light from the excitation unit can be ameliorated or suppressed.

The pulse laser disclosed in the present specification includes a laser medium, a charge storage unit, a power source unit configured to supply an electrical charge to the charge storage unit, an excitation unit configured to cause irradiation of the laser medium with excitation light by being supplied the electrical charge stored in the charge storage unit, a switching unit configured to repeatedly supply the charge stored in the charge storage unit to the excitation unit, an energy monitoring unit configured to monitor energy stored in the charge storage unit, and a control unit configured to prevent the switching unit from supplying the electrical charge stored in the charge storage unit to the excitation unit when the energy monitored by the energy monitoring unit is larger than a threshold.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIGS. 7A through 7C are diagrams illustrating the configuration and operation of a time detecting circuit according to the Second Embodiment.

DESCRIPTION OF THE EMBODIMENTS

Figure 1:
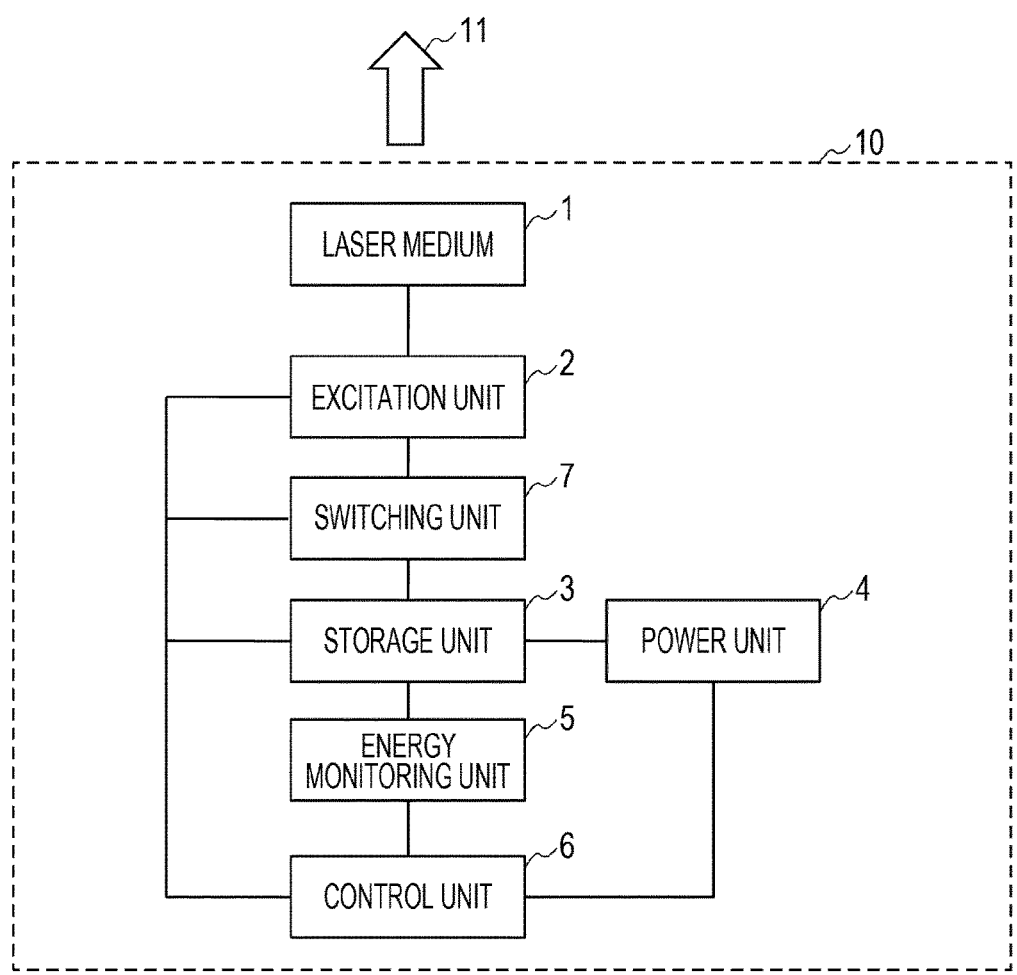
FIG. 1 is a block configuration diagram of a pulse laser according to the present embodiment.

A pulse laser 10 according to the present embodiment will be described with reference to FIG. 1. The pulse laser 10 includes a laser medium 1, an excitation unit 2, a storage unit 3, a power unit 4, an energy monitoring unit 5, a control unit 6, and a switching unit 7 to switch between supplying and not supplying energy stored in the energy unit 3 to the excitation unit 2.

First, an electrical charge is stored in the storage unit 3 by supplying an electrical charge to the storage unit 3 from the power unit 4. Next, excitation light is repeatedly irradiated from the excitation unit 2 to the laser medium 1 by the switching unit 7 repeatedly supplying the charge stored in the storage unit 3 to the excitation unit 2. A laser light 11 is repeatedly emitted from the pulse laser 10 by exciting the laser medium 1 with the excitation light irradiated from the excitation unit 2.

In this way, the intensity of the light emitted from the laser medium 1 can be estimated on the basis of the energy typically stored in the storage unit 3. If a capacitance C for the storage unit 3 is assumed to be constant, the intensity of the light emitted from the laser medium 1 can be estimated on the basis of the electrical charge typically stored in the storage unit 3. For example, the relationship between the amount of the electrical charge previously measured and the intensity of the emitted light can be estimated.

According to the present embodiment, the energy stored in the storage unit 3 is monitored by the energy monitoring unit 5. The energy monitoring unit 5 can estimate the energy stored in the storage unit 3 by monitoring the terminal voltage value for the storage unit 3, the time to supply the electrical charge from the power unit 4 to the storage unit 3, the current value from the power unit 4 to the storage unit 3, or the like. Other devices than can monitor the energy stored in the storage unit 3 can be implemented as the energy monitoring unit 5.

The control unit 6 controls the intensity of the laser light 11 emitted from the pulse laser 10 on the basis of the electrical charge amount monitored by the energy monitoring unit 5. That is to say, the control unit 6 controls the switching unit 7 so that the electrical charge is not supplied from the storage unit 3 to the excitation unit 2 when the energy monitored by the energy monitoring unit 5 is larger than a threshold. As will be described in a subsequent embodiment, the control unit 6 controls the electrical charge to not be supplied by turning off the drive to a thyristor functioning as the switching unit 7, or by interrupting the electrical connection between the storage unit 3 and the excitation unit 2. Other devices than can control the supply of electrical charges from the storage unit 3 to the excitation unit 2 can be used for the configuration of the switching unit 7. The control unit 6 can also control the supply of electrical charges from the storage unit 3 to the excitation unit 2 by any valid method.

Incidentally, when the repeated pulse light is emitted via light produced repeatedly by the excitation unit 2 at a high frequency, it becomes difficult to shield the pulse light by closing a light-shielding portion provisioned to the pulse laser 10 after the light is emitted by the excitation unit 2. However, according to the present embodiment, the control unit 6 can control the supply of electrical charges from the storage unit 3 to the excitation unit 2 on the basis of the energy stored in the storage unit 3. For this reason, the intensity of the light 11 emitted from the pulse laser 10 is estimated and then controlled so that light is not emitted at an unexpected intensity before an electrical charge is supplied from the storage unit 3 to the excitation unit 2, that is to say, before light is emitted by the excitation unit 2. The emission of the repeating pulse light includes the periodic repeating of emitting the pulse light. For example, this includes repeatedly emitting pulse light at a repeating frequency of at least 10 Hz. Similarly, the supply of the repeating electrical charge from the storage unit 3 to the excitation unit 2 includes the periodic supply of electrical charges at a repeating frequency of at least 10 Hz, for example.

The pulse laser according to the present embodiment monitors multiple indexes to estimate the electrical charge amount, and when even one index does not satisfy predetermined conditions, it is preferable to perform control to not emit laser light. This is because failures in the pulse laser that cannot be detected by one index might be detected by another index. For this reason, when performing control on the basis of only certain indexes, laser light might be emitted when a failure has occurred that cannot be detected by these indexes, which could result in the emission of undesired laser light. Therefore, according to the pulse laser according to the present embodiment, it is preferable that the configuration detect failures for many areas on the basis of different indexes.

Therefore, according to the embodiments described later, the energy monitoring unit 5 monitors different indexes such as the terminal voltage value for the storage unit 3, the electrical charge amount supplied from the power unit 4 to the storage unit 3, the time to supply the electrical charge from the power unit 4 to the storage unit 3, or the like. The control unit 6 performs control by independently evaluating each of the multiple indexes against thresholds set for each of the multiple indexes, and emitting laser light when predetermined conditions are satisfied for all indexes. Conversely, the control unit 6 performs control to not emit laser light when the predetermined conditions are not satisfied for even one of the multiple indexes. For example, the control unit 6 performs control to not emit light from the pulse laser 10 when the terminal voltage value for the storage unit 3 is larger than a first threshold or the time to supply the electrical charge to the storage unit 3 is longer that a second threshold. As another example, the control unit 6 performs control to not emit light from the pulse laser 10 when the terminal voltage value for the storage unit 3 is larger than the first threshold or when the electrical charge amount supplied to the storage unit 3 is larger than a third threshold.

The control unit 6 preferably controls the intensity of the light 11 emitted from the pulse laser 10 to be within a predetermined range. It is preferable to set this predetermined range depending on the irradiation subject. As previously described, for example, the predetermined range can be set to no more than the MPE when the measured subject is a biological subject. The predetermined range is more preferably set depending on constraints due to the device configuration. For example, it is more preferable to set the predetermined range in accordance with the rating of the light intensity from the optical system guiding the light 11 emitted from the pulse laser 10 to the measured subject. The predetermined range can be set when shipping, or it can be set by the user.

The control unit 6 can control the intensity of the light emitted from the laser medium 1 by controlling the drive of the excitation unit 2. The control unit 6 can control the intensity of light emitted from the pulse laser 10 by controlling the drive of the light-shielding portion that shields at least a portion of the light emitted from the laser medium 1. The control unit 6 can perform any kind of control as long as it can control the intensity of the light emitted from the pulse laser 10.

According to such a pulse laser regarding the present embodiment, power does need to be preemptively input to the excitation unit to control the emission of light, which enables the suppression of undesired light emitted by the excitation unit and the control of light emitted from the pulse laser.

First Embodiment

According to the First Embodiment, an example will be described in which the terminal voltage value for a capacitor 110 functioning as the storage unit is monitored, and the electrical charge stored by the capacitor 110 is monitored on the basis of the monitored voltage. The pulse laser according to the First Embodiment controls the drive of a shutter 125 functioning as the light-shielding unit and the drive of a flash lamp 116 functioning as the excitation unit on the basis of the electrical charge amount, which is based on the terminal voltage value. According to the present embodiment, the configuration to monitor the electrical charge stored in the capacitor 110 by monitoring the terminal voltage value of the capacitor 110 is collectively referred to as an energy monitoring unit.

If the terminal voltage value of the capacitor 110 is designated as $V_C$, and the capacity of the capacitor 110 is designated as $C_C$, an electrical charge $Q_C$ stored in the capacitor 110 can be expressed by the following Expression 1.

$$Q_C = C_C \cdot V_C \qquad \text{Expression (1)}$$

As can be seen from this expression, there is a proportional relationship between the electrical charge amount $Q_C$ stored in the capacitor 110 and the terminal voltage value $V_C$ of the capacitor 110. The capacity $C_C$ of the capacitor 110 is known from the configuration, and so if the terminal voltage value $V_C$ of the capacitor 110 is monitored, the electrical charge amount $Q_C$ stored in the capacitor 110 can be monitored.

In addition, it is also possible to estimate the relationship between the electrical charge amount $Q_C$ stored in the capacitor 110 and the intensity of the light emitted from a laser head 104. For this reason, by monitoring the terminal voltage value $V_C$ of the capacitor 110, the intensity of the light emitted from the laser head 104 can be estimated. The pulse laser according to the present embodiment is based on these ideas.

Figure 2:
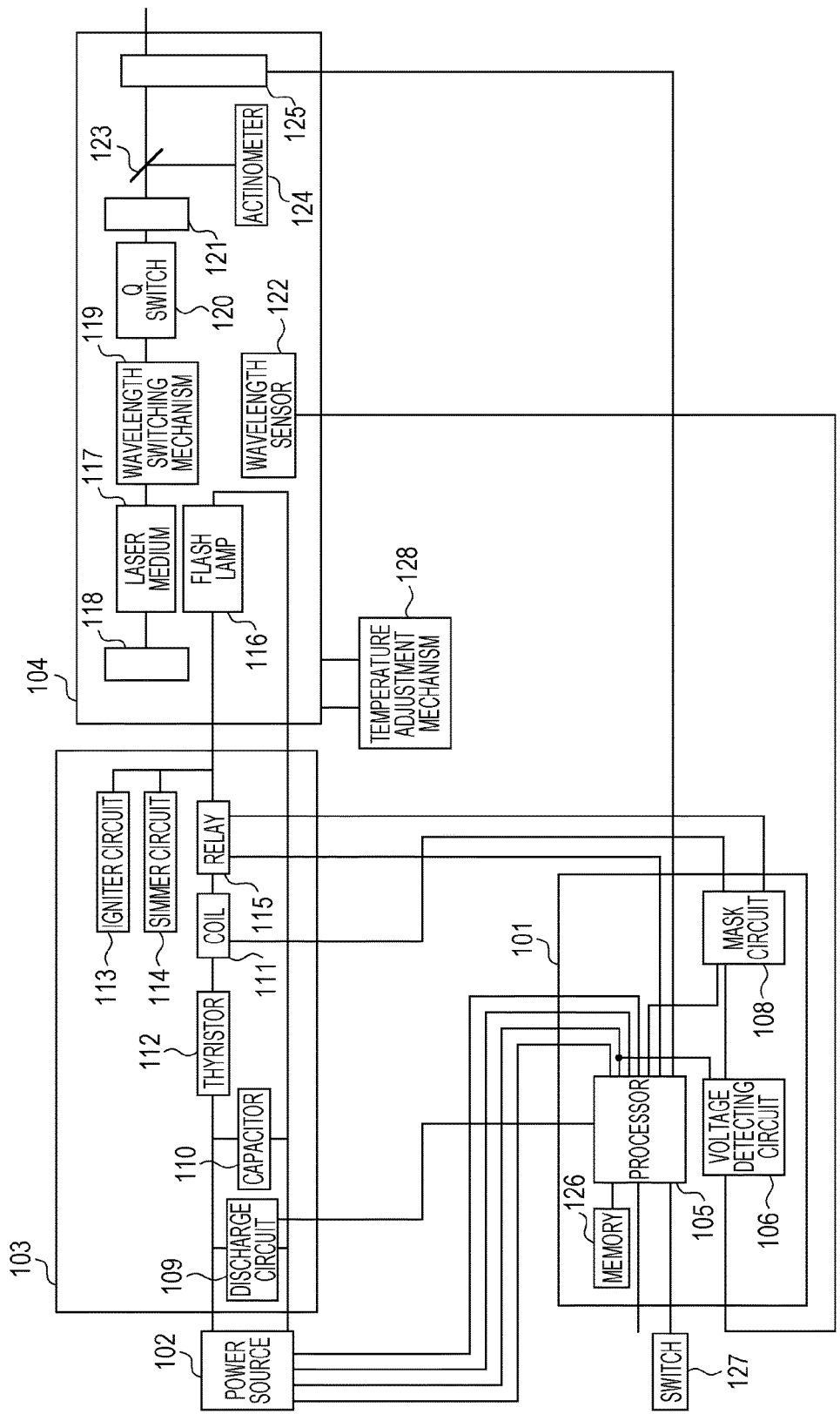
FIG. 2 is a block configuration diagram of a pulse laser according to a First Embodiment.

FIG. 2 is a block diagram of a pulse laser according to the present embodiment.

The pulse laser according to the present embodiment includes a laser controller 101, a power source 102 as the power source, a pulse forming network 103, and the laser head 104 as the main configuration elements. Hereinafter, the pulse forming network is referred to as the PFN.

The laser controller 101 includes a processor 105 as the control unit, a voltage detecting circuit 106, a mask circuit 108, and a memory 126. The laser controller 101 controls the power source 102, the PFN 103, and the laser head 104. The laser controller 101 can received operation commands from a user, and can be connected to a host controller and operates according to instructions from the host controller.

The power source 102 is a variable voltage power source that supplies electrical charges to the capacitor 110. The power source 102 is provisioned with functions to supply an electrical charge to the capacitor 110 at a constant rate until the terminal voltage value of the capacitor 110 reaches a set voltage on the basis of instructions from the laser controller 101. The power source 102 is provisioned with functions to output a signal representing the terminal voltage value of the capacitor 110 to the laser controller 101. The terminal voltage value of the capacitor 110 is a high voltage value and is monitored by dividing the voltage. As previously described, the terminal voltage value of the capacitor 110 is proportional to the electrical charge stored in the capacitor 110. For this reason, the monitoring of the terminal voltage value of the capacitor 110 is equivalent to monitoring the electrical charge stored in the capacitor 110, and so the power source 102 corresponds to a voltage monitoring unit according to the present embodiment.

The PFN 103 includes a discharge circuit 109 functioning as an electrical charge reducing unit, the capacitor 110, a coil 111, a thyristor 112, an igniter circuit 113, a simmer circuit 114, and a relay 115. The PFN 103 accumulates electrical charges from the power source 102, and generates high voltage pulses for lighting the flash lamp 116.

The laser head 104 includes the flash lamp 116, a laser medium 117, a reflecting mirror 118, a wavelength switching mechanism 119, a Q switch 120, an output mirror 121, a wavelength sensor 122, a beam splitter 123, an actinometer 124 functioning as a light intensity receiving unit, and the shutter 125 functioning as the light-shielding unit. The light emitted from the laser head 104 becomes the light emitted by the pulse laser.

The processor 105 controls the power source 102, the pulse forming network 103, and each sensor and actuator in the laser head 104. The processor 105 is a semiconductor chip formed from a microcontroller and peripheral circuits, and performs emission control, changing of parameters such as the amount of light and wavelength, setting and monitoring of the power voltage, and disconnects during failures on the basis of software running on the chip.

The voltage detecting circuit 106 obtains information on the terminal voltage value of the capacitor 110, and sends a disconnect signal to the processor 105 when this exceeds the first threshold. The voltage detecting circuit 106 can set the threshold differently in accordance with the laser light wavelength being prepared for output. Details on the voltage detecting circuit 106 will be described later.

The mask circuit 108 controls the drive of the flash lamp 116 and the shutter 125 on the basis of the disconnect signal from the voltage detecting circuit 106. As a result, the intensity of light emitted from the laser head 104 can be controlled. The mask circuit 108 is a control unit according to the present embodiment similar to the processor 105. Details on the mask circuit 108 will be described during the detailed description of the voltage detecting circuit 106.

The discharge circuit 109 shortens the relay on the basis of the control signal from the processor 105, and can discharge the electrical charge in the capacitor 110. As a result, the electrical charge amount stored in the capacitor 110 can be reduced.

The capacitor 110 stores electrical charges for lighting the flash lamp 116. Film capacitors for high voltage having large capacitance are used for the capacitor 110.

The coil 111 shapes the pulse current waveform from capacitor 110.

The thyristor 112 functioning as the switching unit controls the supply of electrical charges stored in the capacitor 110 to the flash lamp 116 on the basis of the control signal from the processor 105.

The igniter circuit 113 applies high voltage to the flash lamp 116 and forms a conductive path on the basis of the control signal from the processor 105. The igniter circuit 113 is formed from a high voltage DC-DC converter and a current limiting resistor, for example.

The simmer circuit 114 sends a constant auxiliary current to the flash lamp 116 for maintaining the conductive path formed at the flash lamp 116. The simmer circuit 114 is configured from a constant current circuit and a diode for preventing reverse flow, for example.

The relay 115 functioning as a switching unit relays high voltage to disconnects the thyristor 112 from the flash lamp 116 while the igniter circuit 113 is applying high voltage to the flash lamp 116. The processor 105 sends a control signal to the thyristor 112 when the relay 115 is shortened to supply the flash lamp 116 with the electrical charge stored in the capacitor 110 and light the flash lamp 116. That is to say, the relay 115 controls the electrical connection between the capacitor 110 and the flash lamp 116.

The flash lamp 116 is an excitation unit which converts the electrical charge supplied from the capacitor 110 to excitation light and irradiates the excitation light onto the laser medium 117 to excite the laser medium 117.

The laser medium 117 is a solid-state laser crystal such as anyttrium aluminum garnet (YAG), titanium sapphire, or alexandrite. The laser medium 117 is preferably disposed near the flash lamp 116.

A Fabry-Perot resonator is configured with the reflecting mirror 118 and the output mirror 121.

The wavelength switching mechanism 119 selects the resonant wavelength from multiple wavelengths. The wavelength switching mechanism 119 is configured from a birefringent filter and a drive motor, for example. One resonant wavelength from multiple wavelengths that moves the birefringent filter can be selected on the basis of a control signal from the processor 105. According to the present embodiment, a case in which one of two types of wavelengths is selected will be described. The two types of wavelengths described later are referred to as a first wavelength and a second wavelength, respectively.

The Q switch 120 is an electro-optical element that performs Q switching on the basis of a control signal from the processor 105.

The wavelength sensor 122 outputs a signal for notifying the wavelength selected by the wavelength switching mechanism 119 to the processor 105 and the voltage detecting circuit 106. The wavelength sensor 122 outputs, for example, voltage at a high level when the position of the wavelength switching mechanism 119 corresponds to the first wavelength, and outputs a voltage at a low level when the position corresponds to the second wavelength. The wavelength sensor 122 is installed to the wavelength switching mechanism 119.

The beam splitter 123 splits a portion of the laser light output via the output mirror 121 and inputs this incident light to the actinometer 124. Most of the light travels in a straight line, which is incident to the shutter 125.

The actinometer 124 measures the light intensity of the laser light for each pulse, and notifies the measuring result to the processor 105. According to the present embodiment, the actinometer 124 is disposed to be able to detect a portion of the laser light even when the shutter 125 is closed. The actinometer 124 is formed with a pyroelectric sensor or a photodiode and an amplifier circuit, for example.

The shutter 125 functioning as the light-shielding unit controls the emission of laser light toward the exterior of the laser head 104 on the basis of a control signal from the processor 105. Any object that can shield at least a portion of the laser light can be used as the shutter 125. The light-shielding method can be any valid method such as reflection or absorption.

The memory 126 is nonvolatile memory that stores various settings parameters. For example, the memory 126 stores the corresponding relationship between the electrical charge amount stored in the capacitor 110 previously measured for each wavelength and the intensity of the light emitted from the pulse laser. The voltage values that the power source 102 outputs corresponding to theses electrical charges are also stored in the memory 126. As a result, the processor 105 can select from the memory 126 the voltage value that should be set for the power source 102 if the user specifies the wavelength and intensity of the emitted light.

The processor 105 can also calculate the voltage value and electrical charge amount to be set using a logical equation and information on the wavelength and intensity of the emitted light specified by the user.

A switch 127 is paired with a key used to start the pulse laser.

A temperature adjustment mechanism 128 stabilizes the temperature around the laser medium 117. For example, the temperature adjustment mechanism 128 is provisioned with a pump to circulate water at a constant temperature throughout the chassis containing the laser medium 117 and the flash lamp 116. The temperature adjustment mechanism 128 is also internally provisioned with a temperature controller, thermometer, cooling fan, and a heater to circulate water at a constant temperature. The temperature controller sets the temperature of the circulating water by the thermometer, and controls the heater and cooling fan to maintain the water temperature constant.

Figure 3:
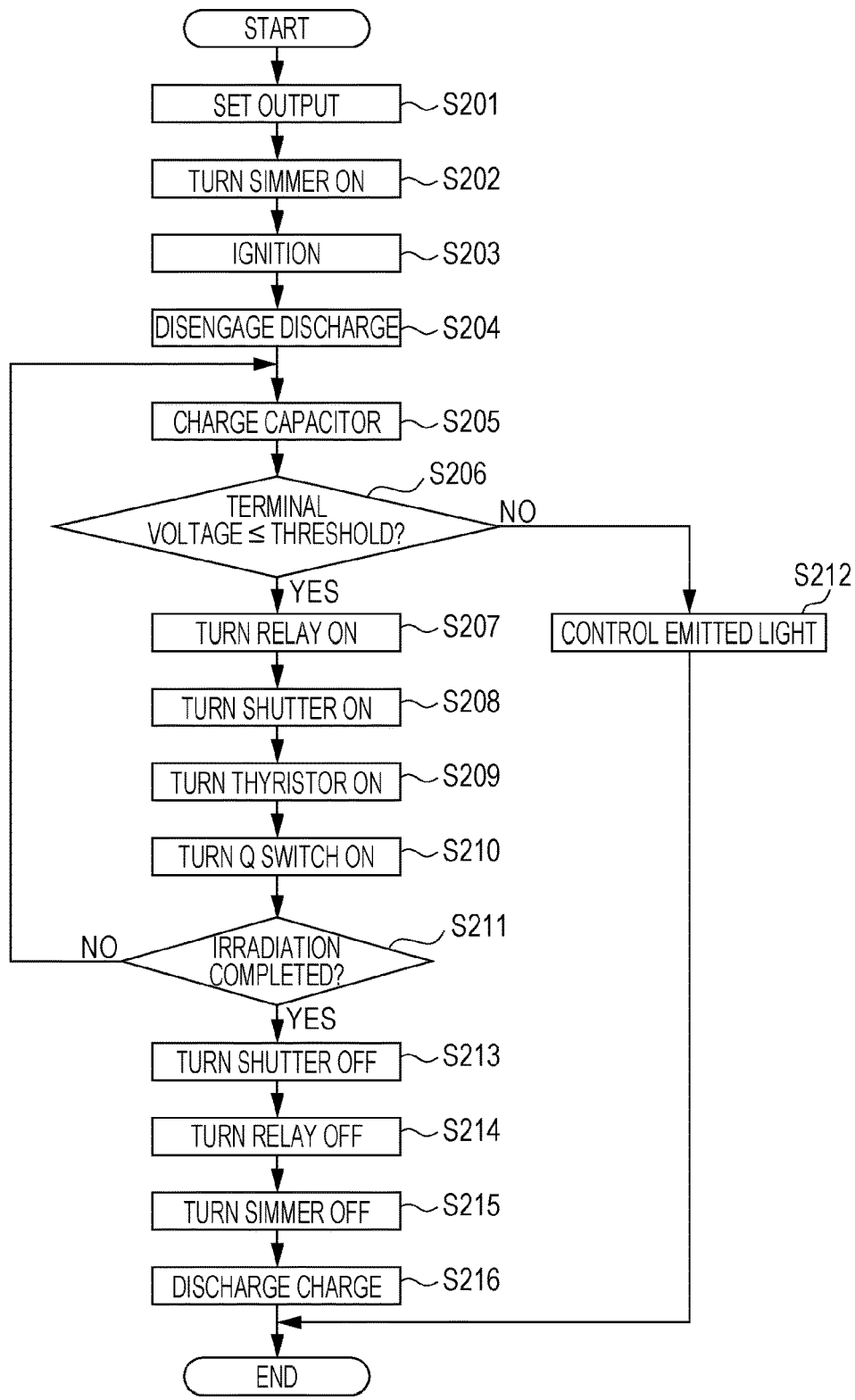
FIG. 3 is a flowchart illustrating the operation of the laser according to the First Embodiment.

FIG. 3 is a flowchart illustrating the operation of the pulse laser according to the present embodiment.

After the light source starts when the user turns the key into the switch 127, at step S201, the processor 105 reads the wavelength and intensity for the emitted light set by the user, and sets the voltage value for the power source 102. The relationship between the intensity of the emitted light and the voltage is recorded to the memory 126. The processor 105 sends control instructions to the wavelength switching mechanism 119 on the basis of the wavelength set by the user, and selects the birefringent filter for outputting the set wavelength. After the operation of the wavelength switching mechanism 119 is finished, a signal representing the wavelength selected is output to the laser controller 101 from the wavelength sensor 122. At step S201, the processor 105 reads the number of repetitions of the pulse light set by the user and stores this internally.

Next, at step S202, the processor 105 sends a control signal to the simmer circuit 114, and then starts the output of current from the simmer circuit 114 to the flash lamp 116. However, a conductive path is not yet formed with the flash lamp 116 at this time, and so most of the simmer current does not flow.

Next, at step S203, the processor 105 sends a control signal to the igniter circuit 113 to apply high voltage to the flash lamp 116. As a result, the flash lamp 116 discharges, which forms a conductive path internally, and the current output from the simmer circuit 114 starts flowing to the flash lamp 116.

Next, at step S204, the processor 105 sends a control signal to the discharge circuit 109 to discharge the relay in the discharge circuit 109. As a result, the positive terminal and the negative terminal of the capacitor 110 are discharged so that an electrical charge can be stored in the capacitor 110.

Next, at step S205, the processor 105 sends a control signal to the power source 102 to supply the electrical charge at regular intervals from the power source 102 to the capacitor 110. As a result, electrical charges are stored in the capacitor 110 at regular intervals and the terminal voltage value gradually increases in the capacitor 110.

At step S206, the processor 105 determines whether or not the terminal voltage value of the capacitor 110 is within the range previously stored in the memory 126 on the basis of the signal representing the terminal voltage value for the capacitor 110 output from the power source 102. According to the present embodiment, only the upper limit for the terminal voltage value of the capacitor 110 is set in the memory 126, but the lower limit can also be set. In this case, the predetermined range is the upper limit and the lower limit of the terminal voltage values for the capacitor 110. The upper limit of the terminal voltage value for the capacitor 110 can be the applied voltage set for the power source 102. The upper limit of the terminal voltage value for the capacitor 110 can be calculated from the upper limit of the intensity of the emitted light set by the processor 105.

According to the present embodiment, the terminal voltage value for the capacitor 110 is compared with the threshold voltage stored in the memory 126, and if the terminal voltage value for the capacitor 110 is at or below the threshold voltage, processing proceeds to step S207. If the terminal voltage value for the capacitor 110 is at or below the threshold, laser light can be emitted at an intensity within a predetermined range.

Conversely, if the terminal voltage value for the capacitor 110 is higher than the threshold, the intensity of the light emitted from the laser head 104 has the potential to be outside of the predetermined range. For this reason, processing proceeds to step S212 to control the intensity of the laser light. Details of the step S212 will be described later.

As previously described, the terminal voltage value of the capacitor 110 is proportional to the electrical charge stored in the capacitor 110. For this reason, the comparison between the terminal voltage value for the capacitor 110 and the threshold voltage at step S206 is equivalent to the comparison between the electrical charge amount stored in the capacitor 110 and the threshold. Details on the threshold using at step S206 will be described later.

Different thresholds for each wavelength are stored in the memory 126 so that these different thresholds can be used in accordance with the set wavelength. This is because the efficiency in lighting the laser head 104 is different depending on the wavelength, and so the electrical charge amount to be stored in the capacitor 110 differs even if outputting laser light at the same intensity. According to the present embodiment, this luminous efficiency indicates the ratio between the electrical charge amount stored in the capacitor 110 and the intensity of light emitted from the laser head 104.

At step S207, the processor 105 sends a control signal to the relay 115 to shorten the distance between the coil 111 and the flash lamp 116. That is to say, the relay 115 electrically connects the capacitor 110 and the flash lamp 116. As a result, the electrical charge can be supplied from the capacitor 110 to the flash lamp 116.

Next, at step S208, the processor 105 sends a control signal to the shutter 125 to open the shutter 125 to emit light from the laser head 104 toward the exterior. In this case, the first few pulses are emitted with the shutter closed so that the intensity of the laser light can be measured by the actinometer 124. The processor 105 reads the measuring result of the actinometer 124, confirms that the light intensity is stable and within the predetermined range stored in the memory 126, and then opens the shutter 125. Laser light is emitted with the shutter 125 closed to confirm the light intensity via commands from the user or a host controller, but the light can also be prevented from emitting to the exterior of the laser head 104.

Next, at step S209, the processor 105 sends a control signal to the thyristor 112 to turn the thyristor on. As a result, the distance from the capacitor 110 to the flash lamp 116 is connected by the coil 111. The electrical charge stored in the capacitor 110 is supplied to the flash lamp 116 to light the flash lamp 116. The excitation light from the flash lamp 116 is absorbed by the laser medium 117 resulting in excitation of the laser medium 117.

Next, at step S210, the processor 105 sends a control signal to a Q switch driver circuit (not illustrated) a few hundred microseconds after exciting the laser medium 117 (specifically, a few hundred microseconds after lighting the flash lamp 116) to set the Q switch 120 previously in a state having a large loss to a state having a small loss. This is performed by changing the terminal voltage value of the Q switch 120 from high voltage to low voltage. As a result, rapid laser oscillation occurs causing a giant pulse to be output form the output mirror 121.

Next, at step S211, the processor 105 determines whether or not the laser has lighted for the number of repetitions set at step S201. If this has completed, processing proceeds to step S213. Conversely, if this has not yet completed, processing returns to step S205 to store an electrical charge in the capacitor 110 again.

At step S213, the processor 105 sends a control signal to the shutter 125 to close the shutter.

Next, at step S214, the processor 105 sends a control signal to the relay 115 to release the thyristor 112 and the flash lamp 116. That is to say, the relay 115 electrically disconnects the capacitor 110 and the flash lamp 116. As a result, the electrical charge cannot be supplied from the capacitor 110 to the flash lamp 116.

Next, at step S215, the processor 105 sends a control signal to the simmer circuit 114 to stop output of the auxiliary current to the flash lamp 116.

Next, at step S216, the processor 105 sends a control signal to the discharge circuit 109 to shorten distance between terminals of the capacitor 110 via the current limit resistor. As a result, the electrical charge remaining in the capacitor 110 is discharged.

The steps S213 through S216 can be performed in any order.

As previously described, if the electrical charge amount of the capacitor 110 is higher than the threshold, that is to say, if it has been determined that the terminal voltage value for the capacitor 110 is higher than the threshold at step S206, processing proceeds to step S212. At step S212, the processor 105 controls the configurations using the method described below so that light is not emitted from the laser head 104.

At step S212, the processor 105 sends a control signal to the relay 115 to open the distance between the thyristor 112 and the flash lamp 116. That is to say, the relay 115 electrically disconnects the capacitor 110 and the flash lamp 116. As a result, the electrical charge stored in the capacitor 110 cannot be supplied to the flash lamp 116.

According to the present embodiment, the relay 115 functioning as the switching unit controls the supply of electrical charges from the capacitor 110 to the flash lamp 116 by shortening and opening, but the control of the supply of electrical charges is not limited to this method. For example, a semiconductor switch functioning as the switching unit can be used. If using such a switching unit, the electrical connection between the capacitor 110 and the flash lamp 116 can be switched by connecting via a low resistance and connecting via a high resistance. For this reason, the supply of electrical charges from the capacitor 110 to the flash lamp 116 can be easily controlled, which enables the electrical charge amount supplied to the flash lamp 116 to be controlled. In addition, instead of controlling the relay 115, the drive signal from the thyristor 112 can be masked enabling the thyristor 112 to be equivalently turned on and off.

According to the present embodiment, the example described uses the thyristor 112 functioning as an element to control the supply of electrical charges to the flash lamp 116, but the type of element is not limited to a thyristor. For example, an element such as an insulated-gate bipolar transistor (IGBT) or metal-oxide-semiconductor field-effect transistor (MOSFET) that can be turned off by a processor can be used, in which case, an off signal can be sent from the processor 105 at step S212.

As step S212, the processor 105 sends a control signal to the discharge circuit 109 functioning as the electrical charge amount reducing unit to shorten the distance between the terminals of the capacitor 110 via the current limit resistor in the discharge circuit 109. That is to say, the discharge circuit 109 reduces the electrical charge stored in the capacitor 110. As a result, the electrical charge amount stored in the capacitor 110 is reduced, which reduces the electrical charge amount that can be supplied to the flash lamp 116.

At step S212, the processor 105 sends a control signal to the power source 102 to reduce the supply of electrical charges from the power source 102 to the capacitor 110. The processor 105 preferably stops the supply of electrical charges from the power source 102 to the capacitor 110. As a result, the storage of electrical charges in the capacitor 110 can be further suppressed. For this reason, reduction of the electrical charge amount can be efficiently performed by the discharge circuit 109.

At step S212, the processor 105 can reduce the light emitted from the laser head 104 by closing the shutter 125 functioning as the light-shielding unit. The shutter 125 can reduce the light emitted from the laser head 104 as long as it can shield at least a portion of the light emitted from the laser medium 117. However, when monitoring the light emitted from the laser head 104 by detecting the oscillated laser light via the actinometer 124, the shutter 125 is preferably provisioned with an external resonator. That is to say, this is preferably disposed so that at least a portion of the light emitted from the output mirror 121 can be shielded.

At step S212, the processor 105 can control only a portion of the previously described controls to prevent light from being emitted from the laser head 104. The present invention is not limited to the previously described controls, and so any control can be used as long as it prevents light from being emitted from the laser head 104.

When laser light is continuously emitted from the laser head 104 by continuously lighting the flash lamp 116, it is difficult to close the shutter 125 after lighting the flash lamp 116 to shield the light. For this reason, according to the method disclosed in Japanese Patent Laid-Open No. 63-153875, undesired light has a potential to be emitted to the exterior of the laser head 104. Conversely, according to the present embodiment, the processor 105 can control the intensity of the emitted light on the basis of the terminal voltage value for the capacitor 110. According to this method, the intensity of light emitted from the laser head 104 can be estimated before lighting the flash lamp 116 so that the intensity of the light emitted from the laser head 104 can be kept within a predetermined range even when continuously emitting laser light. The continuous emission of laser light includes the periodic repetition of laser light emission. For example, this includes repeatedly emitting laser light at a repeating frequency of at least 10 Hz, and continuously emitting laser light.

At step S212, the processor 105 can notify the user of information representing the potential for the intensity of the emitted light to exceed the predetermined range. For example, the processor 105 can communicate information by turning on a color lamp of displaying the potential that the intensity of the emitted light to exceed the predetermined range to a display unit (not illustrated). The processor 105 can also communicate information by playing a sound via a speaker (not illustrated) to indicate that the intensity of the emitted light has a potential to exceed the predetermined range. The method used can be any valid method as long as it communicates information to the user. The processor 105 can also communicate to the user that the intensity of the emitted light is within the predetermined range when the electrical charge amount lower than the threshold.

According to the present embodiment, control of the pulse laser finishes after performing the control of emitted light at step S212, but control after step S212 is not limited thusly. For example, when the electrical charge amount in the capacitor 110 is suitable for the target irradiation level at step S212, processing can proceed to step S207 after step S212 to control the emission of light. Processing can also proceed to step S206 after step S212 to perform control of the emission of light for which the intensity is within the predetermined range after being compared again with the threshold.

According to the pulse laser regarding the present embodiment, by monitoring the terminal voltage value for the capacitor 110, undesired light emitted by the laser head 104 can be suppressed, and the intensity of light emitted from the laser head 104 can also be controlled to be within a predetermined range.

Hereafter, the elements configuring the pulse laser according to the present embodiment will be described in detail.

Figure 4:
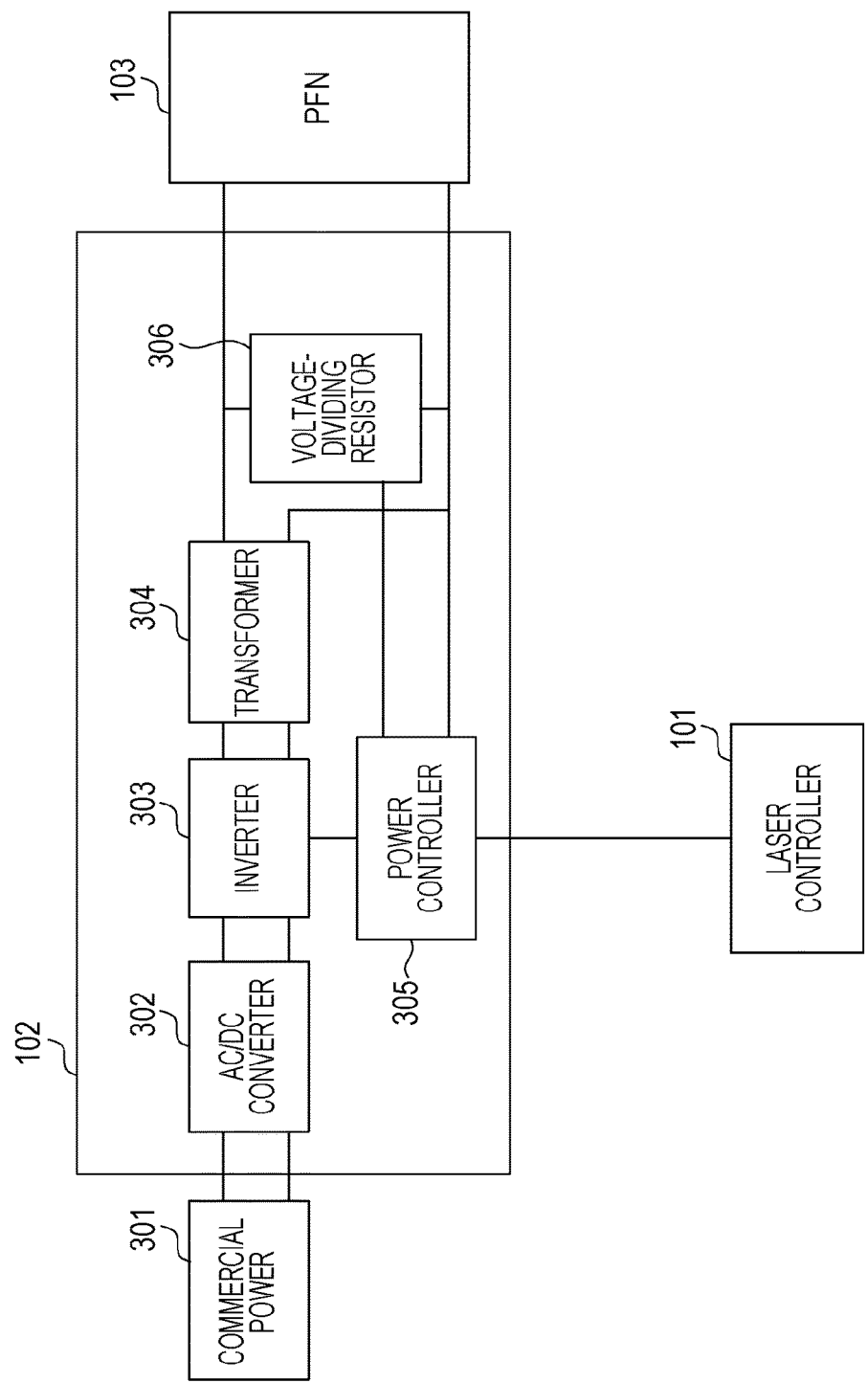
FIG. 4 is a block configuration diagram of a power source according to the First Embodiment.

FIG. 4 is a block diagram illustrating a configuration of the interior of the power source 102.

An AC/DC converter 302 converts 200 VAC power from a commercial power source 301 into direct current. An inverter 303 converts direct current to alternating current. A transformer 304 increases voltage from the inverter 303. A power controller 305 turns on/off a field-effect transistor (FET) (not illustrated) in the inverter 303, and outputs a constant current to the PFN 103 by controlling the duty cycle of the inverter output. A voltage-dividing resistor 306 divides voltage increased by the transformer 304 and provides feedback to the power controller 305.

Next, the threshold voltage corresponding to the terminal voltage value for the capacitor 110 used at step S206 will be described in detail.

According to the present embodiment, a voltage Vm detected by the voltage-dividing resistor 306 with a resistance value R is equivalent to a factor of 1/R regarding the terminal voltage value, and so Vm=Vc/R. The voltage as seen from the processor 105 has a factor of Nc regarding Vm due to the interface and amplifier circuit between the power source 102 and the processor 105.

The maximum allowable intensity of light emitted from the laser head 104 is designated as $E_{max}$, the light-emitting efficiency for the first wavelength is designated as $E_{f1}$, and the light-emitting efficiency for the second wavelength is designated as $E_{f2}$. In this case, a threshold voltage V1 regarding the first wavelength and a threshold voltage V2 regarding the second wavelength are obtained by the following expressions, respectively.

$$V1 = \frac{N_c}{R}\sqrt{\frac{2E_{max}}{C_c E_{f1}}} \qquad \text{Expression (2)}$$

$$V2 = \frac{N_c}{R}\sqrt{\frac{2E_{max}}{C_c E_{f2}}} \qquad \text{Expression (3)}$$

For example, the maximum allowable intensity $E_{max}$ as previously described can be determined on the basis of the MPE. The aforementioned voltages V1 and V2 can be digitized by an AD converter embedded into the processor 105 and stored in the memory 126. As step S206, the processor 105 uses the voltage V1 as the threshold when the selected wavelength is the first wavelength, and uses the voltage V2 as the threshold when the selected wavelength is the second wavelength.

As step S206, the comparison of the terminal voltage value for the capacitor 110 and the threshold voltage performed by the processor 105 can be implemented as different hardware such as the voltage detecting circuit 106.

The operation of the voltage detecting circuit 106 will be described with reference to FIGS. 5A and 5B.

Figure 5A:
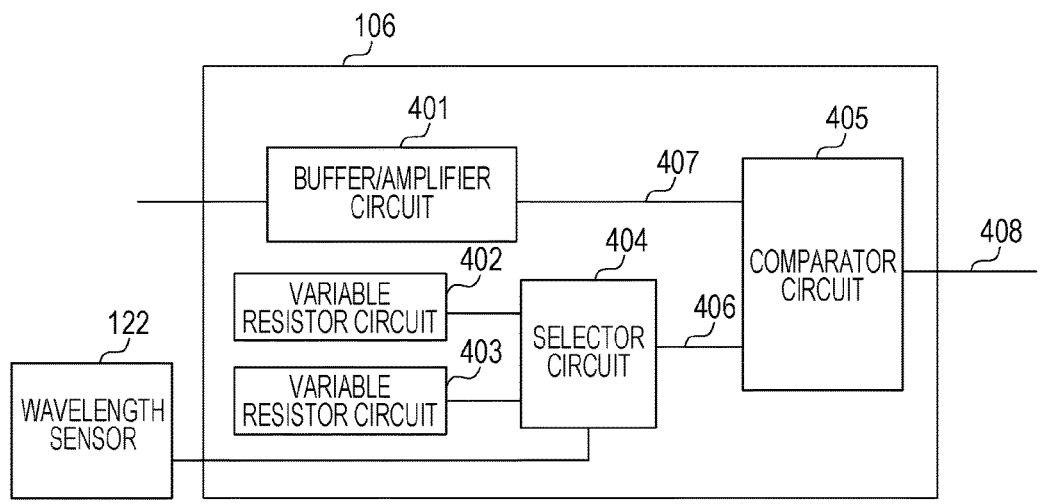
FIGS. 5A and 5B are diagrams illustrating the configuration and operation of a voltage detecting circuit according to the First Embodiment.

FIG. 5A is a block diagram of the interior of the voltage detecting circuit 106. FIG. 5B is a diagram illustrating an example of a waveform used to describe the operation of the voltage detecting circuit 106.

In FIG. 5A, a buffer/amplifier circuit 401 adjusts the current level by receiving a signal representing the terminal voltage value for the capacitor 110 output from the power source 102. The buffer/amplifier circuit 401 is configured, for example, with a voltage follower circuit via an op-amp, an amplifier circuit, and a low-pass filter circuit. The voltage of the output signal from the buffer/amplifier circuit 401 is referred to as a charge voltage 407. The charge voltage 407 represents the electrical charge amount of the capacitor 110.

A variable resistor circuit 402 sets the threshold when oscillating the laser at the first wavelength. The output of the variable resistor circuit 402 is an analog signal indicating the maximum charge which can be stored in the capacitor 110 to output laser of an intensity within a predetermined range at the first wavelength.

A variable resistor circuit 403 sets the threshold when oscillating the laser at the second wavelength. The output of the variable resistor circuit 403 is an analog signal representing the maximum electrical charge amount that can be stored in the capacitor 110 for outputting the laser light at the second wavelength with an intensity that is within the predetermined range.

A selector circuit 404 selects and outputs, of the output voltage from the variable resistor circuit 402 and the variable resistor circuit 403, the output voltage of the variable resistor circuit corresponding to the value of the wavelength sensor 122. The selector circuit 404 is configured with an analog multiplexer, for example. The output voltage from the variable resistor circuit 402 is selected by the selector circuit 404 when the wavelength sensor 122 is indicating the first wavelength. The output voltage from the variable resistor circuit 403 is selected by the selector circuit 404 when the wavelength sensor 122 is indicating the second wavelength. The voltage represented by the signal output from the selector circuit 404 is the threshold voltage. Instead of selecting the signal from the wavelength sensor 122, the selector circuit 404 can select the threshold voltage using a control signal sent by the processor 105 to the wavelength switching mechanism 119.

A comparator circuit 405 compares the charge voltage with the threshold voltage, and outputs voltage at a low level when the charge voltage exceeds the threshold voltage. It outputs voltage at a high level when the charge voltage is at or below the threshold voltage. The signal output by the comparator circuit 405 is referred to as a disconnect signal 408. The disconnect signal 408 is input into the mask circuit 108.

When the disconnect signal from the voltage detecting circuit 106 is at a low level, the mask circuit 108 controls the drive of the flash lamp 116 or the shutter 125 so that the intensity of the light emitted from the laser head 104 is within the predetermined range (step S212). In this case, the mask circuit 108 performs a similar control as the control performed by the processor 105 at step S212 as previously described.

Conversely, when the disconnect signal from the voltage detecting circuit 106 is at a high level, the mask circuit 108 outputs a signal representing that processing is to proceed to step S207 to the processor 105, and then processing proceeds to step S207.

Step S206 can be performed by either or both of the processor 105 and the mask circuit 108.

Figure 5B:
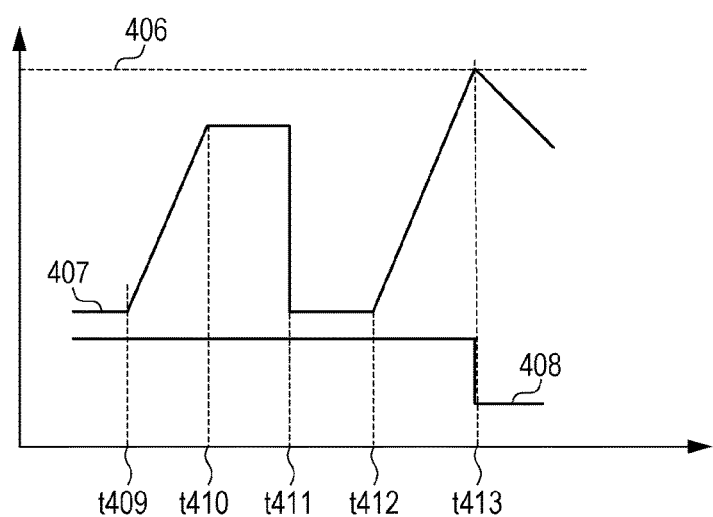

FIG. 5B is a diagram illustrating the voltage waveform of the disconnect signal and the charge voltage during operation of the pulse laser. The horizontal axis represents time, and the vertical axis represents voltage. The vertical axes of the charge voltage and the disconnect signal voltage are spaced apart for the sake of visual clarity.

At a timing t409, the processor 105 outputs the control signal to the power source 102 representing to start storing the charge, and so the charge voltage 407 begins to increase from the timing t409 (step S205). This ratio is proportional to the output current from the power source 102. According to the present embodiment, the power source 102 is a constant power source, and so the charge voltage 407 increases at a constant rate. That is to say, the charge is supplied from the power source 102 to the capacitor 110 at a constant rate.

After the charge voltage 407 reaches the set voltage, the power source 102 stops supplying an electrical charge to the capacitor 110 and also sends a signal representing that storage of the charge is finished to the processor 105. After receiving this, the processor 105 stops the control signal representing to start storing the charge. At a timing t410, the charge voltage 407 has reached the set voltage, which stops the increase of the charge voltage 407.

Next, at a timing t411, the processor 105 turns on the thyristor 112, and the electrical charge in the capacitor 110 flows the to the flash lamp 116 which reduces the charge voltage 407 (step S209).

The timings from t409 to t411 represent the charging and discharging cycle of the capacitor 110, and repeating this cycle at regular intervals generates the pulse light. At the timing t411, the charge voltage 407 is not exceeding a threshold voltage 406, and so the light is emitted from the laser head 104 at an intensity within the predetermined range. At this time, the comparator circuit 405 outputs the disconnect signal 408 to the mask circuit 108 at a high level.

Next, at step S205, the processor 105 outputs again the control signal to the power source 102 representing to start storing a charge, and at a timing t412, the charge voltage starts to increase at a constant rate. Then, at a timing t413, if the charge voltage 407 exceeds the threshold voltage 406 for any reason, the comparator circuit 405 outputs the disconnect signal 408 to the mask circuit 108 at a low level. After receiving the disconnect signal 408 at a low level, the mask circuit 108 controls the drive of the flash lamp 116 or the shutter 125 so that the intensity of the light emitted from the laser head 104 is within the predetermined range (step S212). According to the present embodiment, the discharge circuit 109 reduces the electrical charge amount stored in the capacitor 110 at step S212, which reduces the charge voltage 407.

Next, the threshold used by the voltage detecting circuit 106 will be described. The threshold voltage regarding the first wavelength for the voltage detecting circuit 106 is designated as V3, and the threshold voltage regarding the second wavelength is designated as V4. This is a factor of Ne regarding the signal representing the terminal voltage value of the charge voltage 407 output from the buffer/amplifier circuit 401 to the power source 102. In this case, V3 and V4 are obtained by the following expression, which is similar to that used for V1 and V2.

$$V3 = \frac{N_e}{R}\sqrt{\frac{2E_{1max}}{C_c E_{f1}}} \qquad \text{Expression (4)}$$

$$V4 = \frac{N_e}{R}\sqrt{\frac{2E_{1max}}{C_c E_{f2}}} \qquad \text{Expression (5)}$$

Variable resistors can be previously adjusted so that the voltage output from the variable resistor circuit 402 is V3 and the voltage output from the variable resistor circuit 403 is V4. The selector circuit 404 and the comparator circuit 405 can perform comparisons using the V3 when the wavelength sensor 122 is indicating the first wavelength or the V4 when the wavelength sensor 122 is indicating the second wavelength.

According to the present embodiment, function for monitoring the terminal voltage value for the capacitor 110 and monitoring the electrical charge amount stored in the capacitor 110 can be implemented in multiple configurations. In this case, the multiple configurations are collectively referred to as the energy monitoring unit. That is to say, according to the present embodiment, the power source 102 and the voltage detecting circuit 106 can be designated as the energy monitoring unit.

Second Embodiment

Figure 6:
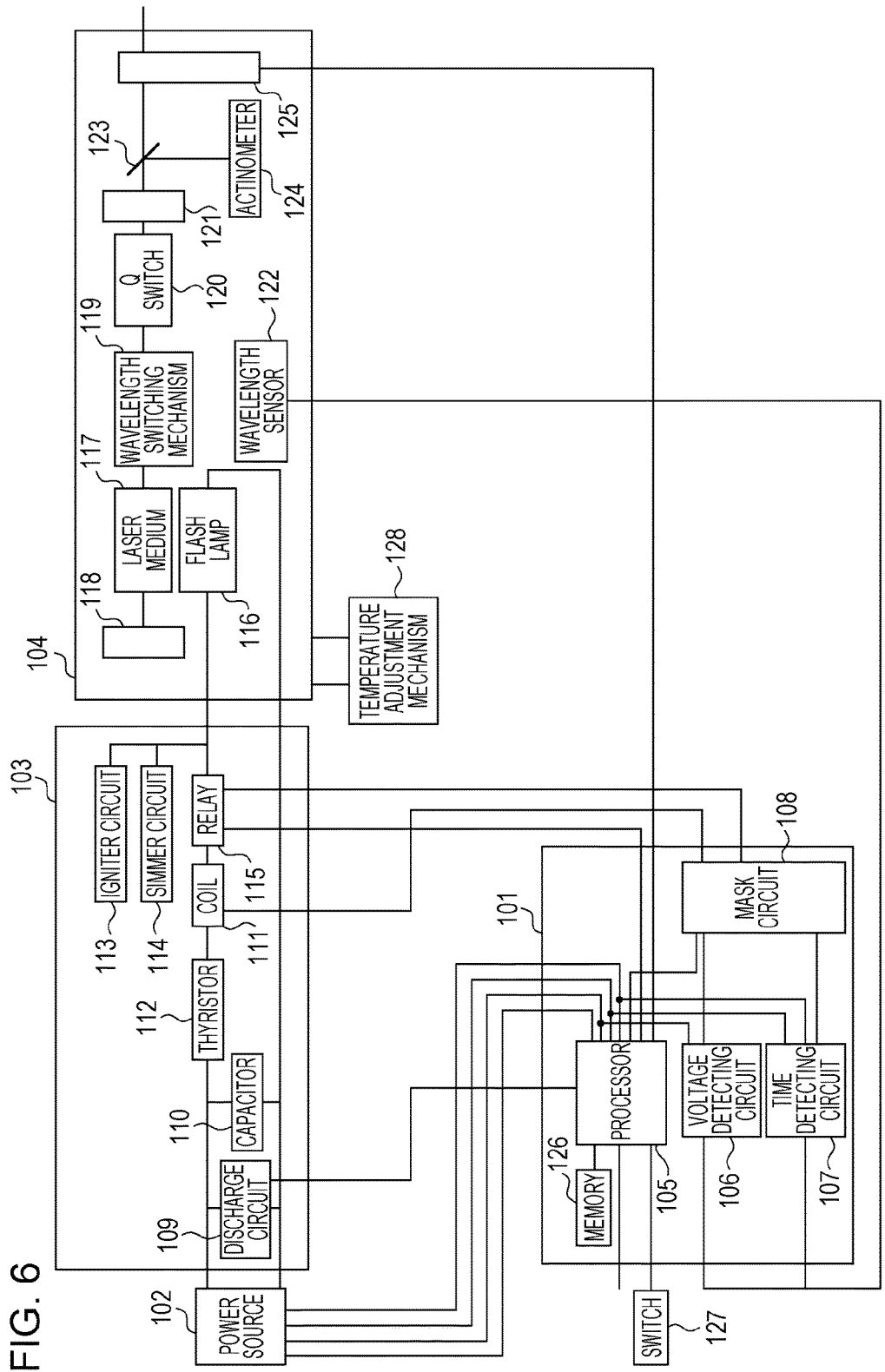
FIG. 6 is a block configuration diagram of a pulse laser according to a Second Embodiment.

Next, the pulse laser according to a Second Embodiment will be described. The pulse laser according to the Second Embodiment as illustrated in FIG. 6 is different from the pulse laser according to the First Embodiment in that it includes a time detecting circuit 107 as a time monitoring unit. The portions of the configuration that are the same as those described regarding the First Embodiment have the same reference numerals and their detailed descriptions are omitted.

The pulse laser according to the Second Embodiment monitors the time to supply an electrical charge to the capacitor 110 in addition to the terminal voltage value for the capacitor 110 monitored as in the First Embodiment. The electrical charge amount stored in the capacitor 110 is estimated on the basis of these monitoring results. The pulse laser according to the Second Embodiment controls the emission of laser light on the basis of both indexes regarding the terminal voltage value for the capacitor 110 and the supply time of the electrical charge.

If the current supplied by the power source 102 to the capacitor 110 is designated as $I_C$ and the time to supply the electrical charge is designated as $T_C$, an electrical charge amount $Q_C$ stored in the capacitor 110 can be expressed by the following Expression 6.

$$Q_c = \int_0^{T_c} I_c \, dt \qquad \text{Expression (6)}$$

It can be seen from this expression that the electrical charge amount $Q_C$ stored in the capacitor 110 can be monitored on the basis of the current $I_C$ and the time $T_C$ to output the current. When the power source 102 functioning as a constant rate power source supplies a constant current to the capacitor 110, the electrical charge amount stored in the capacitor 110 can be monitored on the basis of the time to supply the electrical charge to the capacitor 110. As the current supplied to the capacitor 110 is constant, the electrical charge amount stored in the capacitor 110 can also be monitored on the basis of the time to supply the electrical charge to the capacitor 110.

In addition, it is also possible to estimate the relationship between the electrical charge amount $Q_C$ stored in the capacitor 110 and the intensity of the light emitted from a laser head 104. For this reason, the intensity of the light emitted from the laser head 104 can be estimated by monitoring the time $T_C$ to output the current and the current $I_C$ output to the capacitor 110. The pulse laser according to the present embodiment is based on these ideas.

According to the present embodiment, the time detecting circuit 107 monitors the time to supply the electrical charge to the capacitor 110. As previously described, the monitoring of the time to supply the electrical charge to the capacitor 110 is equivalent to monitoring the electrical charge amount stored in the capacitor 110. For this reason, the time detecting circuit 107 according to the present embodiment can be referred to as the energy monitoring unit.

The operation of the time detecting circuit 107 will be described with reference to FIGS. 7A through 7C. The time detecting circuit 107 is an example of a unit that uses a method different from that of the voltage detecting circuit 106 to monitor the electrical charge amount in the capacitor 110.

Figure 7B:
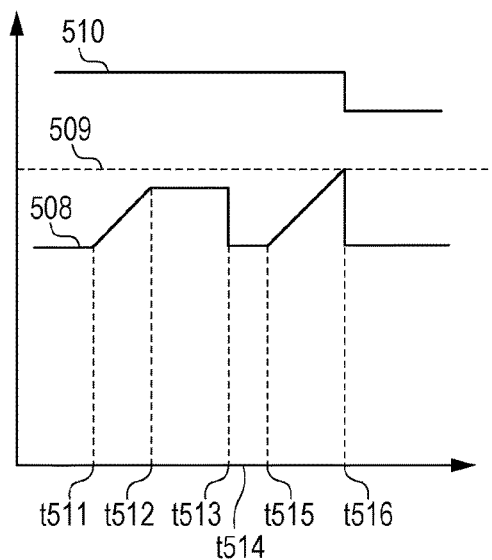
Figure 7C:
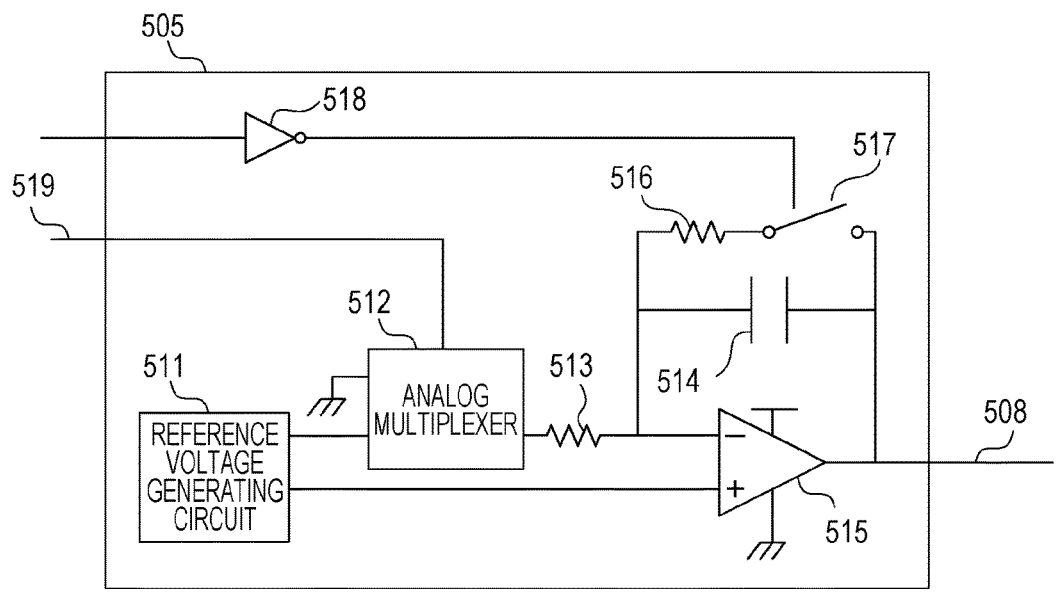

FIG. 7A is a block diagram illustrating the interior of the time detecting circuit 107. FIG. 7B is a diagram illustrating a waveform used to describe the operation of the time detecting circuit 107. FIG. 7C is a block diagram illustrating the interior of a time-voltage conversion circuit 505, which is a configuration element of the time detecting circuit 107.

In FIG. 7A, a pulse forming circuit 501 outputs a signal 519 at a high level during the period when the power source 102 is storing a charge in the capacitor 110, and outputs signal 519 which goes to a low level during the period when not storing the charge. The pulse forming circuit 501, for example, receives the control signal sent from the processor 105 to the power source 102 representing to start storing the charge and the signal sent from the power source 102 representing that the storage of the charge is complete, and then generates a signal at a high level only during the period when storing the charge via a low-pass filter circuit and an AND circuit. The signal output by the pulse forming circuit 501 is input into the time-voltage conversion circuit 505.

A variable resistor circuit 502, variable resistor circuit 503, and selector circuit 504 have the same configuration as the variable resistor circuit 402, variable resistor circuit 403, and selector circuit 404 illustrated in FIGS. 5A and 5B, respectively. The selector circuit 504 outputs a threshold voltage 509. However, the set threshold voltage is different from the example in FIGS. 5A and 5B.

The time-voltage conversion circuit 505 outputs an analog voltage representing the time that the signal 519 from the pulse forming circuit 501 is at a high level. The analog voltage output from the time-voltage conversion circuit 505 is referred to as a time conversion voltage 508. The time-voltage conversion circuit 505 is configured from a reference voltage generating circuit, an integrated circuit with an op-amp and capacitor, and a reset circuit, for example. The time conversion voltage 508 integrates voltage pulses from the reference voltage source when the signal output by the pulse forming circuit 501 is at a high level, and outputs the time conversion voltage 508 representing time. The time-voltage conversion circuit 505 operates the reset circuit when the signal sent by the processor 105 representing to start storing the charge is stopped to reset the integrated voltage. In this way, the time to supply the electrical charge to the capacitor 110 can be monitored by the time-voltage conversion circuit 505.

A comparator circuit 506 compares the time conversion voltage 508 with the threshold voltage 509, and outputs a voltage at a low level when the time conversion voltage 508 exceeds the threshold voltage 509. It outputs a voltage at a high level when the time conversion voltage 508 is at or below the threshold voltage. The signal output from the comparator circuit 506 is input into a storage circuit 507.

The storage circuit 507 outputs voltage at a high level when the output signal from the comparator circuit 506 has never been at a low level, and maintains output of voltage at a low level when this output signal is at a low level at least once. The storage circuit 507 operates during the state in which the key in the switch 127 is turned. The state stored by the storage circuit 507 can be cleared by turning the key in the switch 127 back while the storage circuit 507 maintains output of voltage at a low level. The voltage output from the storage circuit 507 is referred to as a disconnect signal 510. The disconnect signal 510 is input into the mask circuit 108.

The mask circuit 108 controls various configurations in the same as the processor 105 performs controls at the previously described step S212 so that the laser head 104 does not emit light when the disconnect signal 510 from the storage circuit 507 is at a low level, that is to say, when the time to supply the electrical charge to the capacitor 110 exceeds the second threshold. Conversely, the mask circuit 108 controls various configurations so that light is emitted from the laser head 104 when the disconnect signal 510 from the storage circuit 507 is at a high level, that is to say, when the time to supply the electrical charge to the capacitor 110 is at or below the second threshold.

According to the pulse laser regarding the Second Embodiment, by monitoring the time to supply the electrical charge to the capacitor 110, undesired light emitted by the laser head 104 can be suppressed.

FIG. 7B is a diagram illustrating a voltage waveform of the time conversion voltage 508 and the disconnect signal 510 during the operation of the pulse laser. The horizontal axis represents time, and the vertical axis represents voltage. The vertical axes of each signal voltage are spaced apart for the sake of visual clarity.

At timing t511, the processor 105 outputs the control signal to the power source 102 representing to start storing the charge, and so the supply of the electrical charge from the power source 102 to the capacitor 110 starts from the timing t511 (step S205). At this time, the pulse forming circuit 501 outputs the output signal to the time-voltage conversion circuit 505 at a high level. The time-voltage conversion circuit 505 integrates the reference voltage so that the time conversion voltage 508 increases at a constant rate. The charge continues to be stored until the time conversion voltage 508 reaches the voltage indicated by the set storage time.

Then, at a timing t512, the time conversion voltage 508 reaches the voltage indicated by the set storage time, and so the supply of the electrical charge from the power source 102 to the capacitor 110 is stopped. At a timing t513, the processor 105 operates the reset circuit in the time-voltage conversion circuit 505 after stopping the control signal representing to start storing the charge to reset the integrated voltage. Next, at step S209, the processor 105 turns on the thyristor 112, and at a timing t514, the electrical charge in the capacitor 110 is sent to the flash lamp 116 and the electrical charge amount in the capacitor 110 is reduced.

The timings from t511 to t514 represent the charging and discharging cycle of the capacitor 110, and repeating this cycle at regular intervals generates the pulse light. At the timing t513, the time conversion voltage 508 does not exceed the threshold voltage 509, and so light is emitted from the laser head 104 at an intensity that is within the predetermined range at the timing t514. During the cycle of timings t511 through t514, the time conversion voltage 508 does not exceed the threshold voltage 509, and so the disconnect signal 510 stays at a high level.

Next, at a timing t515, the processor 105 outputs again the control signal to the power source 102 representing to start storing a charge, and the charge voltage starts to increase at a constant rate.

At this time, if the storage time for the capacitor 110 lengthens for any reason, the time conversion voltage 508 has a potential to exceed the threshold voltage 509. At a timing t516, the time conversion voltage 508 exceeds the threshold voltage 509, and so the signal output by the comparator circuit 506 changes to a low level, and this state is stored in the storage circuit 507. As a result, the disconnect signal 510 is output to the mask circuit 108 at a low level.

The mask circuit 108 receives the disconnect signal 510 at a low level, and then performs control of various configurations to prevent light from being emitted from the laser head 104 (step S214). The mask circuit 108 can allow light to be emitted after controlling the drive of the flash lamp 116 or the shutter 125 so that the intensity of the light emitted from the laser head 104 is within the predetermined range. According to the present embodiment, the supply of the electrical charge from the power source 102 to the capacitor 110 is stopped at step S212, and so the time conversion voltage 508 is reset.

Conversely, the state in which the time conversion voltage 508 has exceeded the threshold voltage 509 is stored in the storage circuit 507, and so the disconnect signal 510 is maintained at a low level.

Next, the interior of the time-voltage conversion circuit 505 will be described in detail with reference to FIG. 7C.

The time-voltage conversion circuit 505 is configured from a reference voltage generating circuit 511, an analog multiplexer 512, a resistor 513, a capacitor 514, an op-amp 515, a current limiting resistor 516, a normally open semiconductor switch 517, and an inverter circuit 518.

The reference voltage generating circuit 511 outputs a constant voltage Vi. The analog multiplexer 512 selects the voltage Vi from the reference voltage generating circuit 511 when the signal 519 from the pulse forming circuit 501 is at a low level, and selects and outputs a voltage of 0 V when the signal 519 is at a high level.

The output of the analog multiplexer 512 is connected to the reverse input terminal of the op-amp 515 via the resistor 513. The output of the reference voltage generating circuit 511 is connected to the non-inverting terminal of the op-amp 515.

When the electrical charge is supplied from the power source 102 to the capacitor 110, a signal at a low level is input into the control terminal of the semiconductor switch 517 from the inverter circuit 518, and the semiconductor switch 517 opens. When the semiconductor switch 517 opens and the signal 519 is at a high level, the supply of the electrical charge to the capacitor 514 occurs, and the time conversion voltage 508 increases at a constant rate (timings t511 through t512).

Conversely, when the semiconductor switch 517 is open and the signal 519 is at a low level, the supply of the electrical charge to the capacitor 514 stops, and the time conversion voltage 508 does not increase (timings t512 through t513).

When the supply of the electrical charge from the power source 102 to the capacitor 110 stops, a signal at a high level is input into the control terminal of the semiconductor switch 517 from the inverter circuit 518, and the semiconductor switch 517 shortens. At this time, both terminals of the capacitor 514 are shortened, and the electrical charge is reset (timings t513 through t515).

Next, the threshold voltage used by the time detecting circuit 107 will be described.

According to the present embodiment, the power source 102 performs constant current control, and so Qc = IcTc. For this reason, a threshold T5 of the storage time regarding the first wavelength and a threshold T6 of the storage time regarding the second wavelength are obtained with the following expressions.

$$T5 = \frac{1}{I_c}\sqrt{\frac{2E_{1max}C_c}{E_{f1}S}} \qquad \text{Expression (4)}$$

$$T5 = \frac{1}{I_c}\sqrt{\frac{2E_{1max}C_c}{E_{f2}S}} \qquad \text{Expression (5)}$$

Next, if the voltage from the reference voltage generating circuit 511 regarding the integrated circuit of the time-voltage conversion circuit 505 is designated as $V_i$, the resistance of the resistor 513 is designated as $R_i$, and the capacity of the capacitor 514 is designated as $C_i$, a threshold voltage V5 regarding the first wavelength and a threshold voltage V6 regarding the second wavelength can be obtained with the following expressions. However, large values are used for $R_i$ and $C_i$ so that the values of V5 and V6 do not saturate.

$$V5 = V_i\left(1 + \frac{T5}{R_iC_i}\right) \qquad \text{Expression (9)}$$

$$V6 = V_i\left(1 + \frac{T6}{R_iC_i}\right) \qquad \text{Expression (10)}$$

Variable resistors can be previously adjusted so that the voltage output from the variable resistor circuit 502 is V5 and the voltage output from the variable resistor circuit 503 is V6. The selector circuit 504 and the comparator circuit 506 can perform threshold comparisons using the V5 when the wavelength sensor 122 is indicating the first wavelength or the V6 when the wavelength sensor 122 is indicating the second wavelength.

According to the Second Embodiment, the example given uses a circuit to convert the storage time to the capacitor 110 into analog voltage as the method used by the time detecting circuit 107 to detect the time, but the circuit configuration to detect time is not limited thusly. For example, a configuration including a reference clock and counter circuit can be used to count the time for the period in which the pulse forming circuit is outputting a signal at a high level. When the configuration is implemented as a digital circuit, the pulse forming circuit, counter circuit, comparator circuit, and storage circuit can be configured as one FPGA. The storage time for the capacitor 110 can also be monitored by a processor such as a CPU.

According to the Second Embodiment, the example given uses a variable resistor to adjust the threshold of the time detecting circuit 107, but the method to adjust the threshold is not limited thusly. For example, thresholds can be previously written to the memory 126, and the threshold voltage stored in the memory 126 can be generated using a DA converter or similar.

According to the Second Embodiment, the time detecting circuit 107 measures the electrical charge amount supplied to the capacitor 110 on the basis of the storage time under the premise that constant current control is performed by the power source 102. If the power source 102 is not performing constant current control, both the current value output to the capacitor 110 and the storage time are measured, and then this current value and integrated time value are compared with the predetermined thresholds to generate the disconnect signal. Methods to measure current include using a current sensor or measuring the voltage on both ends of a resistor to which stored current flows. Units applied to these methods correspond to a current monitoring unit. The integrated time value based on the detected current value and the storage time corresponds to the electrical charge amount supplied to the capacitor 110. The integrated time value corresponding to this supplied electrical charge amount can be calculated by the processor 105 or the time detecting circuit 107 functioning as an electrical charge amount calculating unit.

According to the Second Embodiment, the processor 105, voltage detecting circuit 106, and time detecting circuit 107 are three mechanisms functioning independently to estimate the electrical charge amount and compare indexes with thresholds, but not all of these mechanisms have to be used. It is possible to use only one of these to compare the electrical charge amount with the threshold. However, as previously described, it is preferable to perform control to prevent laser light from being emitted if even one index does not satisfy predetermined conditions by monitoring multiple indexes for estimating the electrical charge amount. That is to say, the mask circuit 108 preferably performs control so that laser light is not emitted from the laser head 104 when the terminal voltage value for the capacitor 110 is larger than the first threshold or when the storage time to supply the electrical charge to the capacitor 110 is larger than the second threshold. Conversely, the mask circuit 108 preferably performs control to allow laser light to be emitted from the laser head 104 when the terminal voltage value for the capacitor 110 is smaller than the first threshold or when the storage time to supply the electric charge to the capacitor 110 is smaller than the second threshold.

The functions to monitor the time to supply the electrical charge to the capacitor 110 and monitor the electrical charge amount stored in the capacitor 110 can be implemented as multiple configurations. In this case, the multiple configurations are collectively referred to as the energy monitoring unit.

According the First Embodiment and the Second Embodiment, interfaces such as the monitoring signal during operation of the power source 102 and the output complete signal are provisioned, but the present invention is still applicable without these interfaces by provisioning a mechanism such as a voltage dividing resistor in a pulse forming network (PFN) 103.

According to the First Embodiment and the Second Embodiment, two types of wavelengths were described, but the number of wavelengths is not limited thusly. The present invention can be applied to pulse lasers emitted light of three or more wavelengths. The present invention can be applied to variable wavelength pulse lasers in which the wavelength range can be continuously set by setting appropriate thresholds for each wavelength.

Third Embodiment

According to the Third Embodiment, the photoacoustic apparatus to which the pulse laser described regarding the Second Embodiment is applied will be described.

Figure 8:
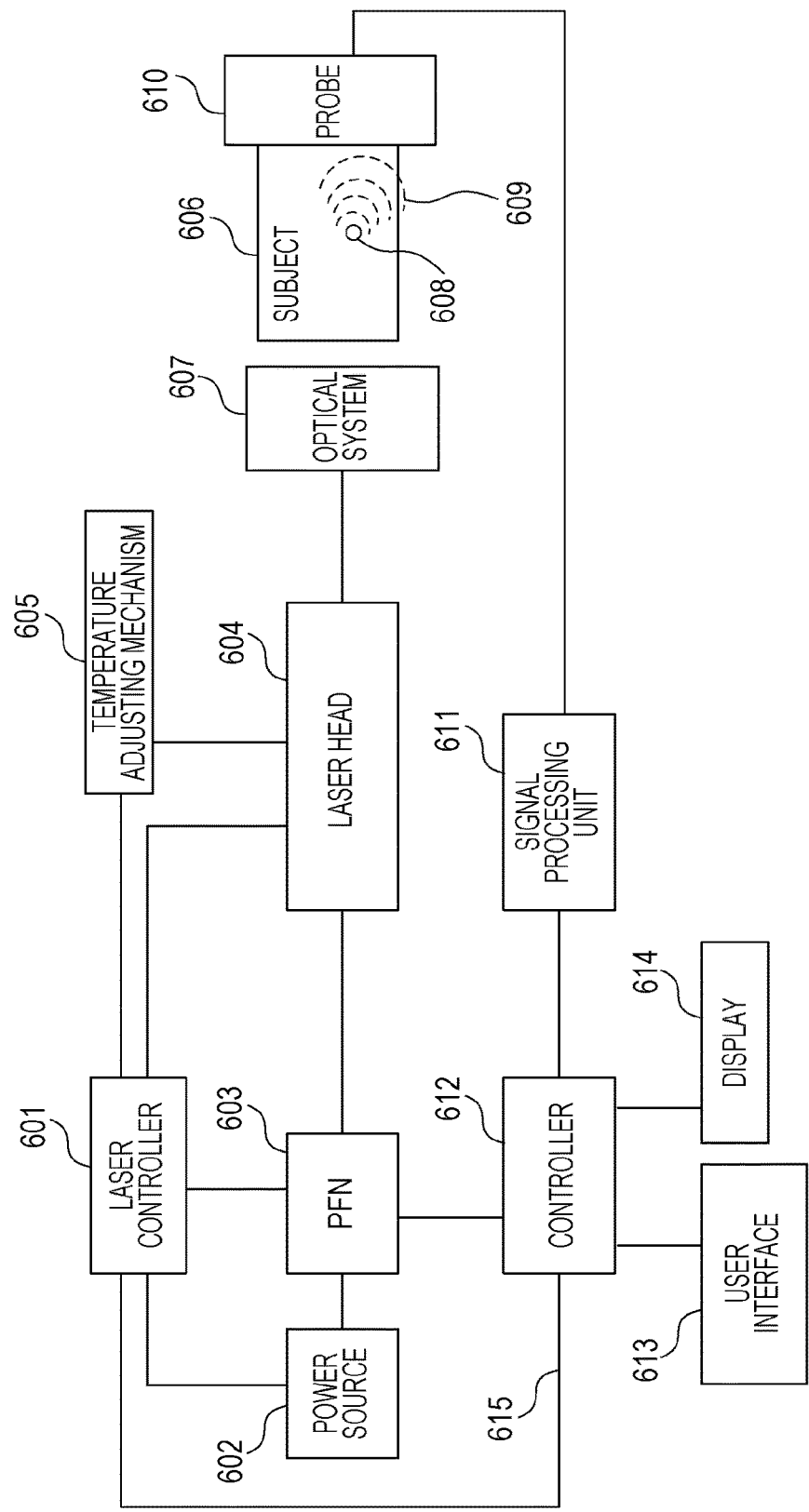
FIG. 8 is a block configuration diagram of a photoacoustic apparatus according to a Third Embodiment.

FIG. 8 is a block diagram of a photoacoustic apparatus according to the present embodiment.

The photoacoustic apparatus according to the present embodiment is configured from a laser controller 601, a power source 602, a PFN 603, a laser head 604, a temperature adjustment mechanism 605, an optical system 607, a probe 610, a signal processing unit 611, a controller 612, a user interface, and a display 614. The laser controller 601, the power source 602, the PFN 603, the laser head 604, and the temperature adjustment mechanism 605 are the same as the laser controller 101, the power source 102, the PFN 103, the laser head 104, and the temperature adjustment mechanism 128 described regarding the Second Embodiment, and so their descriptions are omitted.

A subject 606 is the subject to be measured by the photoacoustic apparatus. The subject 606 is a portion of the subject's body, for example. According to the present embodiment, a breast is used as the subject 606 for the description. The subject 606 is set in a position by a holding mechanism (not illustrated) so that light can be irradiated before being photographed.

The optical system 607 irradiates pulse light onto the measuring site of the subject 606. The optical system 607 is configured, for example, from an optical system that magnifies the light emitted from a laser optical system by a predetermined magnification to adjust the density of the irradiated light and the irradiated region. The light transmitted from the laser head 604 to the optical system 607 is performed by optical fiber or spatial transmission.

A light absorbing member 608 represents an area inside the body of the subject that absorbs a relatively large amount of light, which corresponds to new blood vessels caused by breast cancer, for example. When pulse light is irradiated onto the light absorbing member 608, a photoacoustic wave 609 is generated by the photoacoustic effect.

The probe 610 is provisioned with transducers for receiving the photoacoustic wave 609. The transducers are sensor elements such as lead zirconate titanate (PZT), capacitive micromachined ultrasonic transducers (CMUT), or other disposed in an array, and convert the photoacoustic wave 609 into an electrical signal. According to the present embodiment, this electrical signal is referred to as a photoacoustic signal.

The signal processing unit 611 performs signal processing on the photoacoustic signal from the probe 610. The signal processing unit 611 is configured from a preamp, A/D converter, receiving memory, and afield-programmable gate array (FPGA), for example. The photoacoustic signal is amplified by the preamp in the signal processing unit 611, converted to a digital value by the A/D converter, and then input into the FPGA. The FPGA performs signal processing such as noise reduction processing and phasing. The photoacoustic signal processed by the signal processing unit 611 is stored in memory internal to the signal processing unit 611. According to the present embodiment, the data stored in memory is referred to as photoacoustic signal data. The signal processing unit 611 obtains information on the subject 606 on the basis of the photoacoustic signal data. According to the present embodiment, the information on the subject 606 includes the initial sound pressure of the photoacoustic wave, the optical energy absorption density, the absorption coefficient, and the concentration of the substances configuring the subject 606. The concentration of substances includes the concentration of oxygen saturation, concentration of oxyhemoglobin, concentration of total deoxyhemoglobin and the concentration of total hemoglobin. The concentration of total hemoglobin is the sum of the concentration of oxyhemoglobin and the concentration of deoxyhemoglobin. According to the present embodiment, the information on the subject 606 can be distribution information on each position within the subject instead of just numerical data. That is to say, the information on the subject 606 can be distribution information such as the oxygen saturation distribution and the absorption coefficient distribution.

The controller 612 controls the entire operation of the photoacoustic apparatus, and is configured by a computer and image processing circuit such as a graphics processing unit (GPU). The image processing circuit reads the photoacoustic signal data, performs image reconstruction processing, and generates and displays images representing the absorption coefficient distribution corresponding to the pulse light on the subject 606 on the display 614.

The user interface enables the user to set operating conditions for the photoacoustic apparatus and provide operation start commands. The user interface is configured with a keyboard, mouse, button switch, or other devices. The operating conditions include the measuring range of the subject 606, the measuring time of the photoacoustic signal, or the like. The operation commands include starting the photography of the subject 606, stopping the photography, or the like.

The display 614 displays diagnostic images to the user and notifies the user of the state of the photoacoustic apparatus.

The controller 612 is connected to the laser controller 601 using a communication cable 615, and can perform settings of laser irradiation parameters, irradiation instructions, and status monitoring. The irradiation parameters include the number of pulses of laser light irradiated onto the subject 606, the intensity of the emitted light, wavelength, or the like. The user can set the irradiation parameters via the user interface 613. The content of the irradiation commands include the starting of warm air, the starting of laser irradiation, or the like. The user can control the operation of these pulse laser operations via the user interface. The monitoring of the status can be performed by transmitting the light intensity values for each pulse measured by the actinometer 124 to the controller 612 via the communication cable 615 and using signal correction. The states of the processor 105, the voltage detecting circuit 106, and the time detecting circuit 107 can be transmitted to the controller 612 and then displayed on the display 614.

Figure 9:
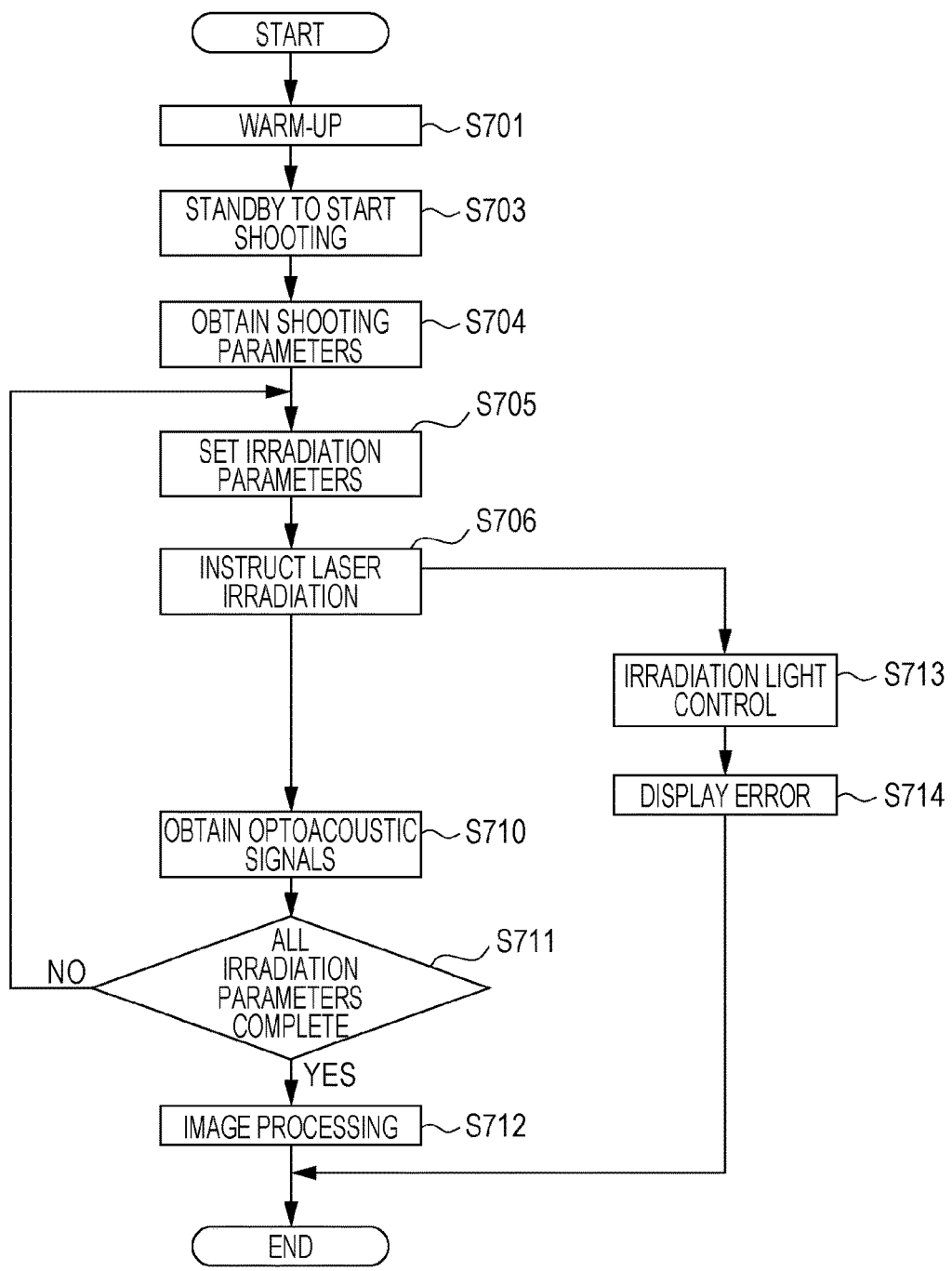
FIG. 9 is a flowchart illustrating the operation of the photoacoustic apparatus according to the Third Embodiment.

FIG. 9 is a flowchart illustrating the operation flow of the photoacoustic apparatus according to the present embodiment.

At step S701, the laser controller 601 starts the warm air process. The laser controller 601 drives the temperature adjustment mechanism 605 to stabilize the temperature of the laser head 604 during this warm air process.

At step S703, the user sets the photographic parameters via the interface 613, and then waits to perform the irradiation start command.

Next, at step S704, the controller 612 stores the photographic parameters in the internal memory. The photographic parameters includes the range to irradiate laser light onto the subject 606, the list of wavelengths of the laser light irradiated, or the like. According to the present embodiment, the irradiated wavelengths include two wavelengths at 756 nm and 797 nm, which are irradiated for 100 pulses. According to the present embodiment, the first wavelength is 756 nm, and the second wavelength is 797 nm.

Next, at step S705, the controller 612 sends the irradiation parameters related to the light source taken from the photographic parameters to the laser controller 601. The irradiation parameters sent to the laser controller 601 this first time includes a wavelength of 756 nm and an irradiation number of 100 pulses.

Next, at a step S706, the controller 612 sends instruction to laser controller 601 to start irradiation of the laser light. As a result, the procedure from steps S201 through S211 as in FIG. 3 cause pulse light of 756 nm wavelengths to be irradiated onto the subject 606 for 100 pulses. Regarding the process at step S706, if the electrical charge amount stored in the capacitor 110 due to power source fluctuations is within the predetermined range, processing proceeds to step S710. If outside the predetermined range, processing proceeds to step S713.

According to the present embodiment, the threshold for the electrical charge amount is set so that the intensity of the emitted light does not exceed the MPE. As a result, it is preferable to perform control to prevent light from being emitted from the pulse laser when light exceeding the MPE from the photoacoustic apparatus has a potential to be irradiated onto the subject. At this time, the photoacoustic apparatus can be controlled so that the intensity of light emitted from the pulse laser is at or below the MPE. The threshold for the intensity of emitted light can be less than the MPE. For example, it is preferable to set the threshold for the electrical charge amount so that the intensity of the emitted light is less than or equal to half of the MPE.

At step S710, the signal processing unit 611 performs signal processing such as amplification, A/D conversion, and noise reduction on the photoacoustic signal for the photoacoustic wave 609 received by the probe generated for each irradiation of the pulse light. The processed result is stored in the internal memory, and then processing proceeds to step S711.

At step S711, the controller 612 determines whether or not the photoacoustic signal for all specified photographic parameters has been obtained. If this is not yet finished, processing returns to step S705, and the instruction is given to the laser controller 601 on the next irradiation parameter. According to the present embodiment, irradiation is performed this first time with a wavelength of 756 nm, and as irradiation at the wavelength of 797 nm has not been performed, processing returns to step S705 to set irradiation parameters of a wavelength of 797 nm and an irradiation number of 100 pulses. Processing proceeds to step S712 after the photoacoustic signal has been obtained at both wavelengths of 756 nm and 797 nm.

At step S712, the controller 612 reads the photoacoustic signal data stored in the memory, performs image processing such as image reconstruction processing, scan conversion processing, or the like, displays the photoacoustic image on the display 614, and then processing ends. At this time, the user can provide instruction using the user interface to display the photoacoustic images of multiple wavelengths side by side, or obtain the oxygen saturation of hemoglobin in the blood from different light absorption distributions for each wavelength and display this on the display.

Conversely, if the electrical charge amount stored in the capacitor 110 is outside the predetermined range, the intensity of the light emitted from the laser head 604 has a potential to be outside the predetermined range. For this reason, at step S713, various configurations are controlled to prevent light from being output from the laser head 604 in the same way as described for step S212.

Next, if the electrical charge amount stored in the capacitor 110 is outside the predetermined range, in conjunction with the control of the intensity of the emitted light, the laser controller 601 displays an error message representing that the intensity of the emitted light has a potential to exceed the predetermined range to the controller 612 at step S714 to notify the user.

According to the present embodiment, control of the photoacoustic apparatus ends after steps S713 and S714, but control is not necessarily limited to ending after steps S713 and S714. For example, control can be performed on the emitted light such that its intensity reaches a target irradiation (intensity at or less than the MPE, for example) at step S713, which then proceeds to step S706 after S714 to control the emission of light.

Thus, according to the photoacoustic apparatus regarding the present embodiment, the generation of undesired light from the pulse laser can be suppressed, and a photoacoustic signal can be obtained.

As illustrated in the First Embodiment and the Second Embodiment, according to the present embodiment, control is performed on the basis of the terminal voltage value for the capacitor 110 or the supplied electrical charge amount in the capacitor 110. For this reason, even if the light is continuously emitted from the pulse laser, the emission of light can be suppressed before light is emitted when there is a potential that the intensity of the emitted light is outside the predetermined range. As a result, the potential for undesired light to be irradiated onto subjects such as biological subjects can be reduced.

According to the present embodiment, control of various configurations is performed by the laser controller 601 and the controller 612, but the present invention is not limited to this configuration, and as such, various configurations can be controlled by only one or three or more controllers.

The signal processing unit 611 can control various configurations. In this case, the photoacoustic apparatus does not need to be provisioned with the laser controller 601 and the controller 612.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-136918, filed Jun. 28, 2013, which is hereby incorporated by reference herein in its entirety.

What is claimed is:

1. A pulse laser arranged to repeatedly emit pulse light, the pulse laser comprising:
   a laser medium;
   a charge storage unit;
   a power source unit configured to supply an electrical charge to the charge storage unit;
   an excitation unit configured to cause irradiation of the laser medium with excitation light by being supplied with an electrical charge stored in the charge storage unit;
   a switching unit connecting to an output of the charge storage unit and configured to control repeated supply of the charge stored in the charge storage unit to the excitation unit;
   an energy monitoring unit configured to monitor energy stored in the charge storage unit; and
   a control unit configured to control the switching unit to prevent the electrical charge stored in the charge storage unit from being supplied to the excitation unit when the energy monitored by the energy monitoring unit is larger than a threshold,
   wherein the threshold is settable such that a value of the threshold differs depends on luminous efficiency of the pulse laser, and
   wherein the luminous efficiency of the pulse laser indicates a ratio between an amount of the electrical charge stored in the charge storage unit and intensity of light emitted from the pulsed laser.

2. The pulse laser according to claim 1,
   wherein the energy monitoring unit includes
      a voltage monitoring unit to monitor the terminal voltage value of the charge storage unit,
   and wherein the control unit is configured to control the switching unit to not supply the electrical charge stored in the charge storage unit to the excitation unit when the terminal voltage value monitored by the voltage monitoring unit is larger than a threshold voltage.

3. The pulse laser according to claim 1,
wherein the power source unit is configured to supply an electrical charge to the charge storage unit at a constant rate,
wherein the energy monitoring unit includes
   a time monitoring unit configured to monitor the time for which the electrical charge is supplied from the power source unit to the charge storage unit,
and wherein the control unit is configured to control the switching unit to not supply the electrical charge stored in the charge storage unit to the excitation unit when the time monitored by the time monitoring unit is larger than a threshold time.

4. The pulse laser according to claim 1,
wherein the energy monitoring unit is configured to monitor a plurality of indexes so as to estimate the energy stored in the charge storage unit,
wherein the control unit is configured to control the switching unit to not supply the electrical charge stored in the charge storage unit to the excitation unit when at least one of the plurality of indexes does not satisfy predetermined conditions.

5. The pulse laser according to claim 4,
wherein the energy monitoring unit includes a voltage monitoring unit configured to monitor the terminal voltage value of the charge storage unit and a time monitoring unit configured to monitor the time for which the electrical charge is supplied from the power source unit to the charge storage unit,
wherein the control unit is configured to control the switching unit to not supply the electrical charge stored in the charge storage unit to the excitation unit when the terminal voltage value is larger than a threshold voltage or the time is larger than a threshold time.

6. The pulse laser according to claim 4,
wherein the energy monitoring unit includes
   a voltage monitoring unit configured to monitor the terminal voltage value of the charge storage unit,
   a current monitoring unit configured to monitor the current value supplied from the power source unit to the charge storage unit,
   a time monitoring unit configured to monitor the time for which the electrical charge is supplied from the power source unit to the charge storage unit, and
   an electrical charge amount calculating unit configured to calculate the electrical charge amount supplied from the power source unit to the charge storage unit on the basis of the current value and time,
wherein the control unit is configured to control the switching unit to not supply the electrical charge stored in the charge storage unit to the excitation unit when the terminal voltage value is larger than a threshold voltage or the supplied electrical charge amount is larger than a threshold electrical charge.

7. The pulse laser according to claim 1,
wherein the control unit is configured to control the power source unit not to supply the electrical charge to the charge storage unit when the energy monitored by the energy monitoring unit is larger than the threshold.

8. The pulse laser according to claim 1, further comprising:
   a light-shielding unit;
   wherein the control unit is configured to control the drive of the light-shielding unit to shield at least a portion of the light emitted from the laser medium when the energy monitored by the energy monitoring unit is larger than the threshold.

9. The pulse laser according to claim 1, further comprising:
   an electrical charge reducing unit configured to reduce the electrical charge stored in the charge storage unit;
   wherein the control unit is configured to control the electrical charge reducing unit so that the energy is at or below the threshold when the energy monitored by the energy monitoring unit is larger than the threshold.

10. The pulse laser according to claim 1,
wherein the switching unit is configured to periodically supply the electrical charge stored in the charge storage unit to the excitation unit.

11. The pulse laser according to claim 10,
wherein the switching unit is configured to supply the electrical charge stored in the charge storage unit to the excitation unit at a repeating frequency of at least 10 Hz.

12. A photoacoustic apparatus comprising:
   the pulse laser according to claim 1;
   a probe adapted to receive a photoacoustic wave generated internally in a body of a subject by irradiating light emitted from the pulse laser onto the subject, and outputting an electrical signal; and
   a signal processing unit adapted to obtain information on the subject on the basis of the electrical signal output from the probe.

13. The pulse laser according to either claim 1,
wherein the luminous efficiency of the pulse laser is a ratio of the electrical charge stored in the charge storage unit to intensity of light emitted from the pulse laser.

14. The pulse laser according to claim 1,
wherein the pulse laser is a variable wavelength laser, and
wherein the threshold is changed for each oscillation wavelength of the pulse laser.

15. The pulse laser according to claim 1, wherein the control unit is arranged to receive information regarding a maximum permissible exposure of a biological subject to be irradiated by the pulse laser.

16. The pulse laser according to claim 1, wherein the threshold is related to the maximum permissible exposure of light emitted to the biological subject and luminous efficiency of the pulse laser.

17. The pulse laser according to claim 1, wherein the control unit is configured to reduce electrical charge stored in the charge storage unit.

18. The pulse laser according to claim 1, wherein the threshold is set such that the intensity of light emitted from the pulse laser does not exceed maximum permissible exposure (MPE).

19. The pulse laser according to claim 1, further comprising a variable resistor circuit configured to set the threshold.

* * * * *